US012594217B2

(12) United States Patent
Shockley, Jr. et al.

(10) Patent No.: US 12,594,217 B2
(45) Date of Patent: Apr. 7, 2026

(54) SELF-CONTAINED PORTABLE POSITIONABLE OSCILLATING MOTOR ARRAY WITH STRAP TENSION SENSING ELEMENTS

(71) Applicant: TACTILE SYSTEMS TECHNOLOGY, INC., Minneapolis, MN (US)

(72) Inventors: Harold David Shockley, Jr., Austin, TX (US); Geoffrey Albert Marcek, Austin, TX (US); Robert Wiley Ellis, Miramar, FL (US)

(73) Assignee: TACTILE SYSTEMS TECHNOLOGY, INC., Minneapolis, MN (US)

( * ) Notice: Subject to any disclaimer, the term of this patent is extended or adjusted under 35 U.S.C. 154(b) by 1184 days.

(21) Appl. No.: 17/328,523

(22) Filed: May 24, 2021

(65) Prior Publication Data

US 2021/0283008 A1 Sep. 16, 2021

Related U.S. Application Data

(63) Continuation-in-part of application No. 14/876,504, filed on Oct. 6, 2015, now Pat. No. 11,013,659.
(Continued)

(51) Int. Cl.
A61H 23/02 (2006.01)
A61B 5/00 (2006.01)
(Continued)

(52) U.S. Cl.
CPC ....... *A61H 23/0236* (2013.01); *A61B 5/4833* (2013.01); *A61H 1/008* (2013.01);
(Continued)

(58) Field of Classification Search
CPC .... A61H 23/00; A61H 23/02; A61H 23/0218; A61H 23/0236; A61H 23/0245;
(Continued)

(56) References Cited

U.S. PATENT DOCUMENTS 3,053,250 A 9/1962 Stubbs
3,310,050 A 3/1967 Goldfarb
(Continued)

FOREIGN PATENT DOCUMENTS

CN 110974244 A * 4/2020 ............. A61B 5/113
DE 202008015893 7/2009
(Continued)

OTHER PUBLICATIONS

English translation for KR 101523846, machine translated by Espacenet.com, translated on Apr. 10, 2025.*
(Continued)

*Primary Examiner* — Tu A Vo
(74) *Attorney, Agent, or Firm* — Mueting Raasch Group

(57) ABSTRACT

A medical device system including a wearable harness worn, during use, on a torso of a subject. Engines coupled to the wearable harness apply an oscillation force to at least one treatment area of the subject in order to mobilize at least some secretions in an airway within the subject substantially adjacent to the at least one treatment area. The wearable harness is secured on the subject using one or more straps coupled to the wearable harness. A controller determines a tension force applied by at least one of the straps by receiving measurements of at least one property from a force sensing element (e.g., a force sensor) integrated with the strap. The tension force may also be correlated to forces being applied to the subject by the engines.

20 Claims, 28 Drawing Sheets

Related U.S. Application Data

(60) Provisional application No. 62/183,819, filed on Jun. 24, 2015, provisional application No. 62/101,131, filed on Jan. 8, 2015, provisional application No. 62/060,772, filed on Oct. 7, 2014.

(51) Int. Cl.

| | |
|---|---|
| *A61H 1/00* | (2006.01) |
| *A61H 23/00* | (2006.01) |
| *A61M 16/00* | (2006.01) |

(52) U.S. Cl.
CPC .......... *A61H 23/006* (2013.01); *A61H 23/02* (2013.01); *A61M 16/0006* (2014.02); *A61B 5/6805* (2013.01); *A61B 2562/0252* (2013.01); *A61H 2201/0111* (2013.01); *A61H 2201/0157* (2013.01); *A61H 2201/0173* (2013.01); *A61H 2201/0192* (2013.01); *A61H 2201/1207* (2013.01); *A61H 2201/1619* (2013.01); *A61H 2201/1621* (2013.01); *A61H 2201/165* (2013.01); *A61H 2201/1652* (2013.01); *A61H 2201/5002* (2013.01); *A61H 2201/5005* (2013.01); *A61H 2201/5007* (2013.01); *A61H 2201/501* (2013.01); *A61H 2201/5023* (2013.01); *A61H 2201/5038* (2013.01); *A61H 2201/5046* (2013.01); *A61H 2201/5061* (2013.01); *A61H 2201/5082* (2013.01); *A61H 2201/5084* (2013.01); *A61H 2201/5097* (2013.01); *A61H 2205/08* (2013.01); *A61H 2205/084* (2013.01); *A61H 2230/50* (2013.01)

(58) Field of Classification Search
CPC ............ A61H 23/0254; A61H 23/0263; A61H 2023/002; A61H 23/04; A61H 2201/1621; A61H 2205/084; A61H 23/006; A61M 16/0006; A61B 2562/0252; A61B 5/4833
See application file for complete search history.

(56) References Cited

U.S. PATENT DOCUMENTS

| | | | |
|---|---|---|---|
| 3,351,053 A | 11/1967 | Stuttle | |
| 3,612,046 A | 10/1971 | Gaylord | |
| 3,885,553 A | 5/1975 | Vecchio ............. A61H 23/0218 601/15 |
| 4,216,766 A | 8/1980 | Duykers et al. | |
| 4,257,408 A | 3/1981 | Ramey .................... A63H 3/48 601/46 |
| 4,354,067 A | 10/1982 | Yamada ............. A61H 23/0236 381/301 |
| 4,979,502 A | 12/1990 | Hunt | |
| 5,235,967 A | 8/1993 | Arbisi et al. | |
| 5,273,028 A | 12/1993 | McLeod | |
| 5,363,863 A | 11/1994 | Lelli et al. | |
| 5,437,617 A | 8/1995 | Heinz et al. | |
| 5,884,338 A | 3/1999 | Golde | |
| 6,152,855 A | 11/2000 | Dean, Jr. | |
| 6,193,678 B1 | 2/2001 | Brannon | |
| 6,329,638 B1 | 12/2001 | Bloodworth | |
| 6,471,663 B1 | 10/2002 | Van Brunt | |
| 6,514,200 B1 | 2/2003 | Khouri | |
| 6,682,494 B1 | 1/2004 | Sleichter, III .......... A61H 23/02 601/57 |
| 6,736,785 B1 | 5/2004 | Van Brunt | |
| 6,926,667 B2 | 8/2005 | Khouri | |
| 6,962,277 B2 | 11/2005 | Quintana et al. | |
| 7,147,610 B2 | 12/2006 | Maalouf | |
| 7,207,953 B1 | 4/2007 | Goicaj | |
| 7,374,550 B2 | 5/2008 | Hansen et al. | |
| 7,618,384 B2 | 11/2009 | Nardi .................... A61B 5/6828 601/101 |

| | | | |
|---|---|---|---|
| 7,890,342 B1 | 2/2011 | Yruko et al. | |
| 7,954,900 B2 | 6/2011 | Shantha et al. | |
| 8,332,236 B2 | 12/2012 | Yurko et al. | |
| 8,460,223 B2 | 6/2013 | Huster et al. | |
| 8,786,999 B2 | 7/2014 | Locke | |
| 8,870,796 B2 | 10/2014 | Hoffmann | |
| 8,950,207 B2 | 2/2015 | Raines et al. | |
| 9,289,350 B2 | 3/2016 | Helgeson et al. | |
| 9,549,869 B2 | 1/2017 | DeViegler et al. | |
| 9,839,553 B2 | 12/2017 | Bannister | |
| 9,895,287 B2 | 2/2018 | Shockley et al. | |
| 9,907,488 B2 | 3/2018 | Barduson | |
| 9,907,725 B2 | 3/2018 | Shockley et al. | |
| 9,956,134 B2 | 5/2018 | Shockley et al. | |
| 9,968,511 B2 | 5/2018 | Huster et al. | |
| 10,034,813 B1 | 7/2018 | Silver | |
| 10,039,692 B2 | 8/2018 | Nickelson | |
| 10,159,623 B2 | 12/2018 | Leftly | |
| 10,251,810 B2 | 4/2019 | Shockley et al. | |
| 10,357,433 B1* | 7/2019 | Feliz .................... G08B 13/149 |
| 11,013,659 B2 | 5/2021 | Shockley et al. | |
| 2002/0013516 A1 | 1/2002 | Freyre et al. | |
| 2003/0028132 A1 | 2/2003 | Bastia et al. | |
| 2003/0199899 A1 | 10/2003 | Boecker | |
| 2004/0039317 A1 | 2/2004 | Souney et al. | |
| 2004/0082237 A1 | 4/2004 | Farmer et al. | |
| 2004/0133133 A1 | 7/2004 | Dreimann et al. | |
| 2004/0158177 A1 | 8/2004 | Van Brunt et al. | |
| 2004/0216943 A1* | 11/2004 | Kwon .................... A61G 5/048 180/316 |
| 2005/0053252 A1 | 3/2005 | Cohen ............... A61H 23/0236 381/333 |
| 2005/0054958 A1 | 3/2005 | Hoffmann ............ A61B 17/225 601/46 |
| 2005/0126578 A1 | 6/2005 | Garrison et al. | |
| 2005/0234372 A1 | 10/2005 | Hansen et al. | |
| 2005/0235988 A1 | 10/2005 | Hansen et al. | |
| 2005/0267387 A1* | 12/2005 | Baldauf ................. A61H 31/02 601/44 |
| 2006/0009684 A1 | 1/2006 | Kim | |
| 2006/0015045 A1 | 1/2006 | Zets et al. | |
| 2006/0075537 A1 | 4/2006 | Tsai | |
| 2006/0218692 A1 | 10/2006 | Lamarque | |
| 2007/0197881 A1 | 8/2007 | Wolf et al. | |
| 2007/0239087 A1 | 10/2007 | Kivisto | |
| 2008/0000477 A1 | 1/2008 | Huster et al. | |
| 2008/0027363 A1 | 1/2008 | Brueckmann ...... A61H 23/0263 601/70 |
| 2008/0086062 A1 | 4/2008 | Hansen et al. | |
| 2008/0108914 A1 | 5/2008 | Brouqueyre et al. | |
| 2008/0275343 A1 | 11/2008 | Hoffman | |
| 2009/0069728 A1 | 3/2009 | Hoffman et al. | |
| 2009/0177222 A1 | 7/2009 | Brown et al. | |
| 2009/0234256 A1 | 9/2009 | Helgeson et al. | |
| 2009/0255022 A1 | 10/2009 | Smith et al. | |
| 2010/0113993 A1 | 5/2010 | Davis et al. | |
| 2010/0292568 A1 | 11/2010 | Droitcour et al. | |
| 2011/0139836 A1 | 6/2011 | Klann | |
| 2011/0162121 A1 | 7/2011 | Klann | |
| 2011/0166486 A1 | 7/2011 | Kumanomido | |
| 2012/0022415 A1 | 1/2012 | Mullen et al. | |
| 2012/0185999 A1 | 7/2012 | Raviv | |
| 2012/0186000 A1 | 7/2012 | Raviv | |
| 2012/0259255 A1 | 10/2012 | Tomlinson et al. | |
| 2012/0291798 A1 | 11/2012 | Park et al. | |
| 2013/0037531 A1 | 2/2013 | Gray .................... H05B 1/0272 219/211 |
| 2013/0211294 A1 | 8/2013 | Bohris | |
| 2013/0261518 A1 | 10/2013 | Hansen et al. | |
| 2013/0267877 A1* | 10/2013 | Van Brunt ........... A61H 9/0007 601/149 |
| 2013/0289455 A1 | 10/2013 | Clapp et al. | |
| 2013/0296056 A1* | 11/2013 | Kaldahl ................. A63F 13/42 463/36 |
| 2014/0005579 A1 | 1/2014 | Drlik et al. | |
| 2014/0012167 A1 | 1/2014 | DeVlieger et al. | |
| 2014/0150791 A1 | 6/2014 | Bimkrant et al. | |
| 2014/0257151 A1 | 9/2014 | Chikkanaravangala et al. | |

(56) References Cited

U.S. PATENT DOCUMENTS

| | | | | |
|---|---|---|---|---|
| 2014/0257153 | A1 | 9/2014 | Nickelson | A61H 23/0263 601/150 |
| 2014/0257156 | A1* | 9/2014 | Capra | A43B 3/34 602/5 |
| 2014/0358189 | A1 | 12/2014 | Mashiach et al. | |
| 2015/0141891 | A1* | 5/2015 | Wang | A61F 5/028 602/19 |
| 2015/0265209 | A1 | 9/2015 | Zhang | |
| 2015/0272236 | A1 | 10/2015 | Chen et al. | |
| 2015/0374578 | A1 | 12/2015 | Matsuura | A61H 23/0263 601/46 |
| 2016/0089571 | A1 | 3/2016 | Wesley et al. | |
| 2016/0095782 | A1 | 4/2016 | Shockley et al. | |
| 2016/0095783 | A1 | 4/2016 | Shockley et al. | |
| 2016/0095790 | A1 | 4/2016 | Shockley et al. | |
| 2016/0095791 | A1 | 4/2016 | Shockley et al. | |
| 2016/0095792 | A1 | 4/2016 | Shockley et al. | |
| 2016/0095793 | A1 | 4/2016 | Shockley et al. | |
| 2016/0306932 | A1 | 10/2016 | Fateh et al. | |
| 2017/0000686 | A1 | 1/2017 | Shockley et al. | |
| 2017/0000687 | A1 | 1/2017 | Shockley et al. | |
| 2017/0095400 | A1 | 4/2017 | Shockley et al. | |
| 2017/0156976 | A1* | 6/2017 | Shockley, Jr. | A61H 23/02 |
| 2017/0177818 | A1 | 6/2017 | Eustis | |
| 2017/0281460 | A1* | 10/2017 | Zgoda | A61H 31/004 |
| 2018/0092801 | A1 | 4/2018 | Shockley et al. | |
| 2019/0038502 | A1* | 2/2019 | Shockley, Jr. | A61H 23/02 |
| 2020/0100981 | A1 | 4/2020 | Bobey et al. | |
| 2020/0129360 | A1* | 4/2020 | Ju | A61H 1/0288 |
| 2021/0212853 | A1* | 7/2021 | Du | H02K 11/20 |

FOREIGN PATENT DOCUMENTS

| | | | | |
|---|---|---|---|---|
| KR | 101523846 | B1 * | 7/2013 | |
| WO | WO 02/053083 | A2 | 7/2002 | |
| WO | WO 2010/071919 | | 7/2010 | |
| WO | WO 2011/094883 | | 8/2011 | |
| WO | WO 2013/052817 | | 4/2013 | |
| WO | WO 2016/057527 | | 4/2016 | |
| WO | WO 2018/093993 | | 5/2018 | |
| WO | WO-2018093993 | A1 * | 5/2018 | A61B 5/055 |

OTHER PUBLICATIONS

European Patent Application No. 22174754.6, filed May 23, 2022; Extended EP Search Report issued Oct. 20, 2022; 10 pages.

Advisory Action for U.S. Appl. No. 14/876,479 mailed on Jul. 1, 2019.

Advisory Action for U.S. Appl. No. 14/876,487 mailed on Oct. 9, 2019.

Advisory Action for U.S. Appl. No. 14/876,494 mailed on Jul. 1, 2019.

Advisory Action for U.S. Appl. No. 16/157,631 mailed on Nov. 21, 2019.

Advisory Action for U.S. Appl. No. 15/728,887 mailed on Nov. 28, 2018.

Afflo Vest, International Biophysics Press Release, PRNewswire, May 11, 2016.

Co-Pending U.S. Appl. No. 15/728,887 entitled, "Systems and Methods or Monitoring a Subject's Effective Use of a Self-Contained Portable Positionable Oscillating Motor Array" to Shockley et al. filed Oct. 10, 2017.

Co-Pending U.S. Appl. No. 15/266,465 entitled, "Self-Contained Portable Positionable Oscillating Motor Array System" to Shockley et al. filed Sep. 15, 2016.

Co-Pending U.S. Appl. No. 15/266,496 entitled, "Method of Clearing a Biological Airway Using a Self-Contained Portable Positionable Oscillating Motor Array" to Shockley et al. filed Sep. 15, 2016.

Co-Pending U.S. Appl. No. 15/266,521 entitled, "Kit for Clearing a Biological Airway Including a Self-Contained Portable Positionable Oscillating Motor Array" to Shockley et al. filed Sep. 15, 2016.

Co-Pending U.S. Appl. No. 15/353,383 entitled, "Systems and Methods for Monitoring a Subject's Effective Use of a Self-Contained Portable Positionable Oscillating Motor Array" to Shockley et al. filed Nov. 16, 2016.

Co-Pending U.S. Appl. No. 16/157,631 entitled: "Systems and Methods for Effective Reuse of a Self-Contained Portable Positionable Oscillating Motor Array" to Shockley et al. filed Oct. 11, 2018.

Co-Pending U.S. Appl. No. 14/876,472 entitled, "Self-Contained Portable Positionable Oscillating Motor Array" to Shockley et al. filed Oct. 6, 2015.

Co-Pending U.S. Appl. No. 14/876,476 entitled, "Method of Clearing a Biological Airway Using a Self-Contained Portable Positionable Oscillating Motor Array" to Shockley et al. filed Oct. 6, 2015.

Co-Pending U.S. Appl. No. 14/876,487 entitled, "Kit for Clearing a Biological Airway Including a Self-Contained Portable Positionable Oscillating Motor Array" to Shockley et al. filed Oct. 6, 2015.

Co-Pending U.S. Appl. No. 14/876,494 entitled, "Flexible Vest Including a Positionable Oscillating Motor Array" to Shockley et al. filed Oct. 6, 2015.

Co-Pending U.S. Appl. No. 14/876,504 entitled, "Self-Contained Portable Positionable Oscillating Motor Array Including Disposable And/Or Recyclable Portions" to Shockley et al. filed Oct. 6, 2015.

Co-Pending U.S. Appl. No. 14/876,507 entitled, "Self-Contained Portable Positionable Oscillating Motor Array Including an Outer Harness Providing a Compressive Force" to Shockley et al. filed Oct. 6, 2015.

Cooper, M. "An evidence-based study of adolescents with cystic fibrosis demonstrated that Afflo Vest® by International Biophysics contributed to improved lung function scores" Chicago, Illinois. Apr. 6, 2015.

Extended European Search Report for European Application No. 15848394.1, mailed May 11, 2018.

Final Office Action for U.S. Appl. No. 15/266,465 mailed on Jul. 3, 2017.

Final Office Action for U.S. Appl. No. 15/266,496 mailed on Jun. 14, 2017.

Final Office Action for U.S. Appl. No. 15/266,521 mailed on Jun. 30, 2017.

Final Office Action for U.S. Appl. No. 14/876,494 mailed on Feb. 21, 2020.

Final Office Action for U.S. Appl. No. 14/876,472 mailed on Mar. 27, 2019.

Final Office Action for U.S. Appl. No. 14/876,472 mailed on Mar. 12, 2020.

Final Office Action for U.S. Appl. No. 14/876,472 mailed on Jun. 14, 2018.

Final Office Action for U.S. Appl. No. 14/876,479 mailed on Apr. 12, 2019.

Final Office Action for U.S. Appl. No. 14/876,479 mailed on Jun. 13, 2018.

Final Office Action for U.S. Appl. No. 14/876,487 mailed on Jul. 29, 2019.

Final Office Action for U.S. Appl. No. 14/876,494 mailed on Apr. 11, 2019.

Final Office Action for U.S. Appl. No. 14/876,504 mailed on Mar. 28, 2019.

Final Office Action for U.S. Appl. No. 15/728,887 mailed on Jun. 13, 2019.

Final Office Action for U.S. Appl. No. 16/157,631 mailed on Jul. 1, 2019.

International Biophysics Corporation AffloVest White Paper, "AffloVest Answering Needs: The Role of the Afflo Vest in the Respiratory Market", Oct. 2013.

International Biophysics Corporation "Clinical Study of the AffloVest as a High Frequency Chest Wall Oscillation Device" Mar. 2013.

International Biophysics Corporation AffloVest Pamphlet. Oct. 2013.

International Search Report and Written Opinion for PCT/US2019/055183 dated Dec. 5, 2019; 11 pages.

International Search Report and Written Opinion for PCT/US17/61935 mailed Feb. 6, 2018. pp. 12.

International Preliminary Report on Patentability for PCT/US17/61935 issued Feb. 14, 2019.

(56) References Cited

OTHER PUBLICATIONS

International Search Report and Written Opinion for PCT/U.S. Pat. No. 15154261 mailed Jan. 7, 2016. pp. 20.
Non-Final Office Action for U.S. Appl. No. 14/876,479 mailed on Oct. 5, 2017.
Non-Final Office Action for U.S. Appl. No. 15/266,465 mailed on Dec. 20, 2016.
Non-Final Office Action for U.S. Appl. No. 15/266,496 mailed on Dec. 2, 2016.
Non-Final Office Action for U.S. Appl. No. 15/266,521 mailed on Dec. 29, 2016.
Non-Final Office Action for U.S. Appl. No. 14/876,479 mailed on Sep. 30, 2019.
Non-Final Office Action for U.S. Appl. No. 14/876,479 mailed on Mar. 13, 2020.
Non-Final Office Action for U.S. Appl. No. 14/876,487 mailed on Feb. 5, 2020.
Non-Final Office Action for U.S. Appl. No. 14/876,487 mailed on Jan. 2, 2019.
Non-Final Office Action for U.S. Appl. No. 14/876,487 mailed on Apr. 6, 2018.
Non-Final Office Action for U.S. Appl. No. 14/876,494 mailed on Sep. 20, 2019.
Non-Final Office Action for U.S. Appl. No. 14/876,472 mailed on Sep. 30, 2019.
Non-Final Office Action for U.S. Appl. No. 14/876,472 mailed on Dec. 15, 2017.
Non-Final Office Action for U.S. Appl. No. 15/728,887 mailed on Oct. 1, 2019.
Non-Final Office Action for U.S. Appl. No. 15/353,383 mailed Feb. 24, 2020.
Non-Final Office Action for U.S. Appl. No. 15/728,887 mailed on Jan. 7, 2019.
Non-Final Office Action for U.S. Appl. No. 15/728,887 mailed on Feb. 28, 2018.
Non-Final Office Action for U.S. Appl. No. 16/157,631 mailed on Jan. 2, 2019.
Non-Final Office Action for U.S. Appl. No. 14/876,507.
Notice of Allowance for U.S. Appl. No. 15/728,887 mailed on Feb. 11, 2020.
Notice of Allowance for U.S. Appl. No. 16/157,631 mailed on May 14, 2020.
Notice of Allowance for U.S. Appl. No. 14/876,507 mailed on Jul. 23, 2018.
Notice of Allowance for U.S. Appl. No. 14/876,507 mailed on Nov. 27, 2018.
Notice of Allowance for U.S. Appl. No. 15/266,465 mailed on Oct. 30, 2017.
Notice of Allowance for U.S. Appl. No. 15/266,496 mailed on Dec. 21, 2017.
Notice of Allowance for U.S. Appl. No. 15/266,521 mailed on Sep. 26, 2017.
Office Action for Australian Application No. 2015328220 issued Jul. 1, 2019.
Office Action for European Application No. 15848394.1 - 1126 issued Apr. 21, 2020.
International Preliminary Report on Patentability for PCT/US2015/054261 mailed Apr. 11, 2017. pp. 18.
Hill-Rom Monarch TM Airway Clearance System Pamphlet "Take More Control of Your Life" Apr. 13, 2017.
Supplemental Search Report for European Application No. 17872163.5 issued on May 8, 2020.
Tackett, M.W. et al., "Lung function improvement with AffloVest® HFCWO use: a clinician's perspective on PFT score data from 25 patients with cystic fibrosis." May 2016.
The Vibra Vest by OxyCare GMbH product brochure. May 2012.

* cited by examiner

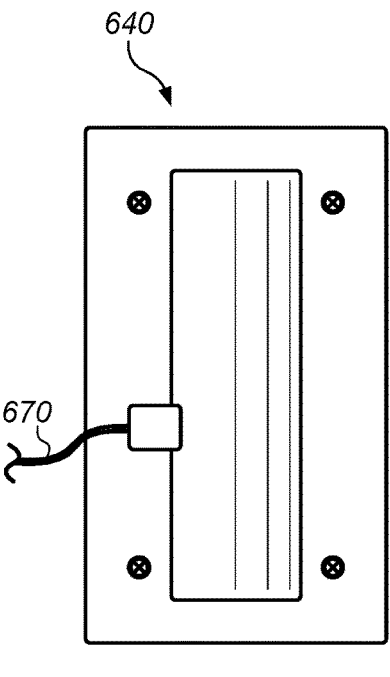
*FIG. 18A*
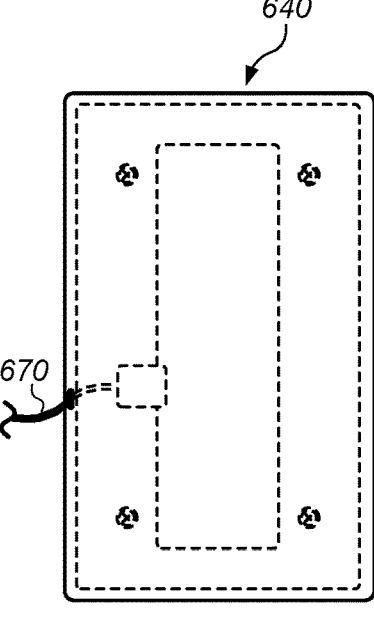
*FIG. 18B*
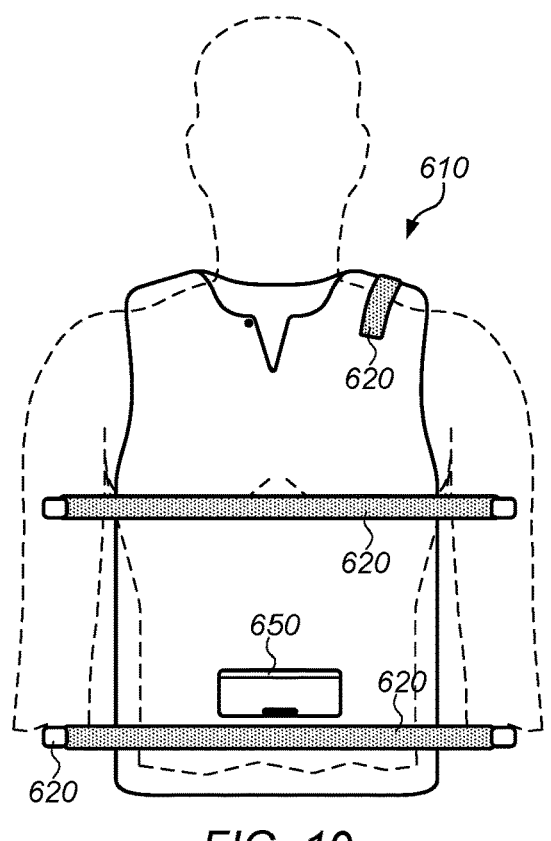
*FIG. 19*
*FIG. 18C*

650

900

660

920

650

665

660

665

660

900

SELF-CONTAINED PORTABLE POSITIONABLE OSCILLATING MOTOR ARRAY WITH STRAP TENSION SENSING ELEMENTS

PRIORITY CLAIM

This application is a continuation-in-part of U.S. patent application Ser. No. 14/876,504 (now U.S. Pat. No. 11,013, 659) entitled "SELF-CONTAINED PORTABLE POSITIONABLE OSCILLATING MOTOR ARRAY INCLUDING DISPOSABLE AND/OR RECYCLABLE PORTIONS", which claims priority to U.S. Provisional Patent Application No. 62/060,772 entitled "CHEST WALL OSCILLATION VEST" filed on Oct. 7, 2014, U.S. Provisional Patent Application No. 62/101,131 entitled "SELF-CONTAINED PORTABLE HIGH FREQUENCY PHYSIOLOGICAL OSCILLATOR" filed on Jan. 8, 2015, and U.S. Provisional Patent Application No. 62/183,819 entitled "SELF-CONTAINED PORTABLE POSITIONABLE OSCILLATING MOTOR ARRAY" filed on Jun. 24, 2015, all of which are incorporated by reference herein.

BACKGROUND OF THE INVENTION

1. Field of the Invention

The present disclosure generally relates to respiratory therapies. More particularly, the disclosure generally relates to a method and system for ensuring a subject's proper use of high frequency upper chest wall oscillation therapy.

2. Description of the Relevant Art

Subjects who are unable to mobilize their own lung secretions without assistance (subjects with, for example, chronic obstructive pulmonary disease (COPD)) are exceedingly common, which together account for over 1 million hospitalizations each year in the United States alone. Beta agonists, anti-cholinergics, and corticosteroids delivered in aerosolized forms are recommended in the treatment of COPD. These medications rely on deposition into distal airspaces to suppress airway inflammation or promote bronchodilation. Excessive mucous production and impaired airway mucociliary clearance can lead to airway plugging, and thereby reduce the deposition of and response to aerosolized medications. These considerations highlight the need for therapies that clear airways of mucus in the acute management of diseases such as cystic fibrosis, bronchiectasis (and other severe form of COPD), and certain neuromuscular diseases.

Manual percussion techniques of chest physiotherapy have been used for a variety of diseases, such as cystic fibrosis, emphysema, and chronic bronchitis, to remove excess mucus that collects in the lungs. To bypass dependency on a caregiver to provide this therapy, chest compression and oscillation devices have been developed to produce High Frequency Chest Wall Oscillation (HFCWO), a very successful method of airway clearance. High frequency chest wall oscillation (HFCWO) creates high velocity, low amplitude oscillation energy when applied through a vest worn over the thorax, and is used for airway mucus clearance in patients with cystic fibrosis, bronchiectasis, and neuromuscular disorders. Studies in patients with cystic fibrosis suggest that HFCWO applied via a vest is as effective as other modes of airway mucus clearance, including hand-held devices (e.g., flutter devices) and conventional chest physiotherapy. HFCWO offers the advantage that it can be performed in acutely ill patients who may be unable to use hand-held devices effectively, such as early in the course of hospitalization. Moreover, HFCWO can be performed without the assistance from trained health care personnel, and may therefore offer a practical advantage compared to chest physiotherapy.

Professional healthcare environments are required to constantly be vigilant regarding sanitation and cross contamination between patients. To this end medical equipment must be sanitized before being used again. However, sanitizing equipment is typically time consuming and/or expensive. As such much of the equipment used in healthcare environments which comes into direct contact with subjects is disposable (or covered by disposable sheaths). It is typically much easier and/or less expensive to throw away equipment which comes into contact with subjects as opposed to cleaning the equipment.

At least in part as a result of rising health care costs, rehabilitation programs are often being performed in a patient's home without a visiting therapist being physically present. However, at-home rehabilitation programs suffer from compliance and monitoring deficiencies. The physical therapist has no way to determine whether the patient followed the rehabilitation program and must rely on the office visit to ascertain progress.

In addition, as many medical devices are prescribed by physicians, the opportunity to collect reliable data is often times limited to those patient visits which occur at prescribed intervals. There are many reasons which make it highly desirable to have accurate patient compliance data for a medical device used on an outpatient basis. One of these reasons includes the desirability of collecting data for a large group of individuals which may then be used to make considered judgments relating to the medical device efficacy and recommended regimen for optimal results. For these kinds of studies, accurate data is imperative. Still another reason for collecting accurate data is that immediate feedback and positive re-enforcement may be provided to the patient encouraging them to follow the regimen. The doctor may use this accurate compliance data in order to correct the patient should she not only under-use but over-use the device in an effort to achieve even greater results by increasing her wearing times beyond that which is recommended. This can help prevent unintended side effects through overuse of any medical device.

However, conventional compliance monitoring systems are deficient in that they measure only the operational usage time. These devices then provide a total usage time, from which the device or a remote computer calculates the compliance with the prescribed total usage time. The measurement and compliance monitoring is a strictly static one demonstrating compliant or non-compliant behavior. Therefore, there remains a need for a method and system for dynamically tracking and monitoring a patient's compliance with a prescribed device usage allotment during a cycle of predetermined periods.

Another deficiency evident in the conventional compliance monitoring methods and systems stems from the definition of "compliance." These systems track, monitor, and manage a "technical" compliance level for a patient. For example, if a patient is prescribed a device usage time of eight hours of usage in a 24-hour period, the mere fact that the patient uses the device for 8 hours during that period does not necessarily indicate that the patient is "compliant." In prior art systems, any usage of the device is accrued towards the prescription level. Conventional compliance monitoring methods may only track whether a medical device is on and not be capable of determining if the subject is actually using the article or using it correctly.

Therefore, there remains a need for a compliance method and system that ensures that the patient is meeting an actual compliance level based upon a prescribed regimen for a medical device and that the medical device is applied effectively.

BRIEF DESCRIPTION OF THE DRAWINGS

Advantages of the present invention may become apparent to those skilled in the art with the benefit of the following detailed description of the preferred embodiments and upon reference to the accompanying drawings.

FIGS. 18A-B depict a first and a second opposing side view of a representation of a first embodiment of an engine.

FIG. 18C depicts a side view of a representation of a second embodiment of an engine.

FIG. 19 depicts a front view of a representation of an embodiment of a portable high frequency chest wall oscillator inner harness including unsecured fasteners positioned on a subject.

US 12,594,217 B2

5

Figure 34:
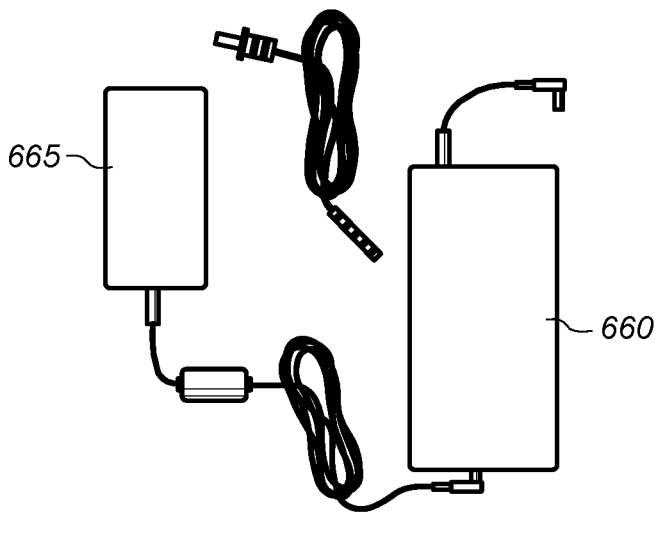

FIG. 34 depicts a representation of an embodiment of a battery and a battery charging system.

Figure 35:
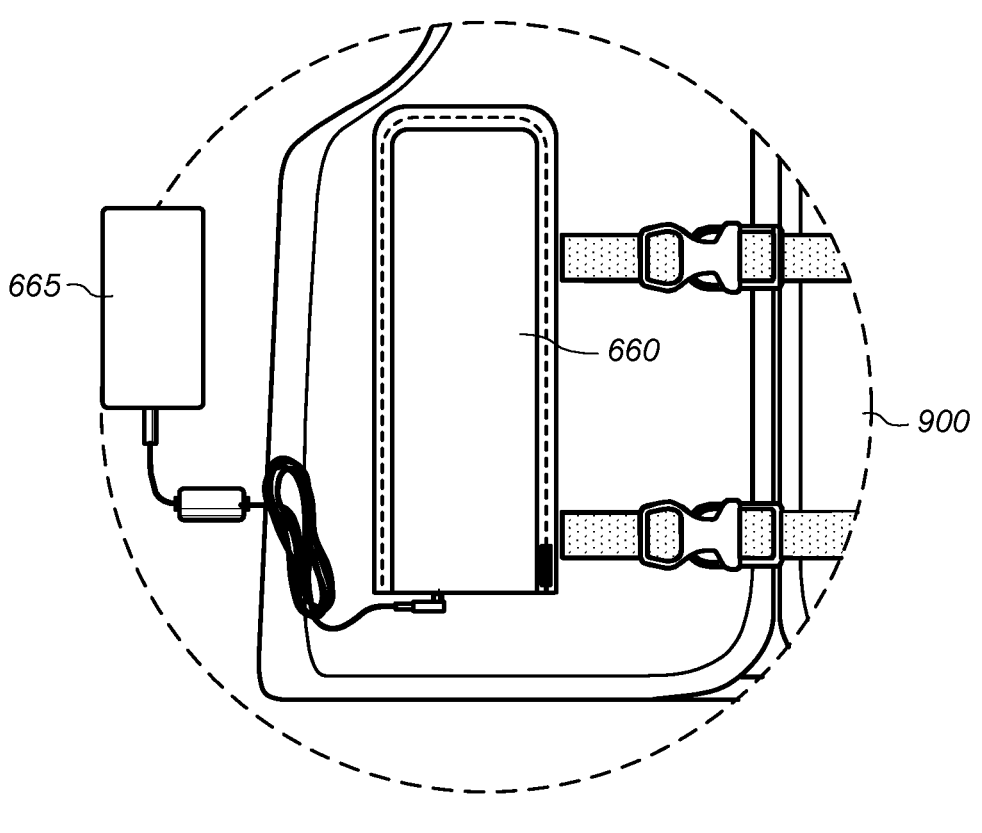

FIG. 35 depicts a representation of an embodiment of a portable high frequency chest wall oscillator wearable harness including a compression mechanism, a battery, a battery charging system.

Figure 36:
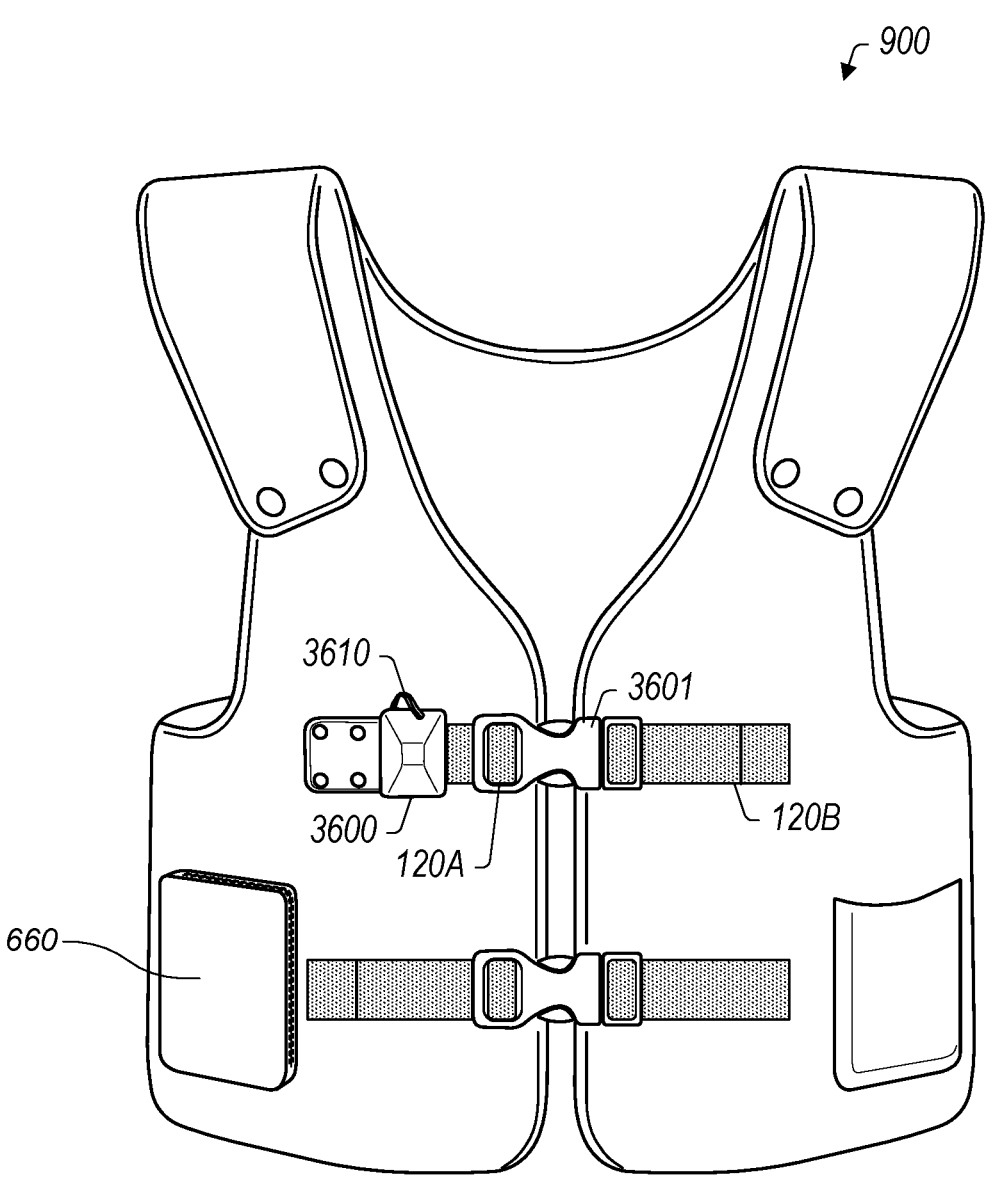

FIG. 36 depicts a representation of an embodiment of a portable high frequency chest wall oscillator wearable harness with a force sensing element integrated with a strap on the wearable harness.

Figure 37:
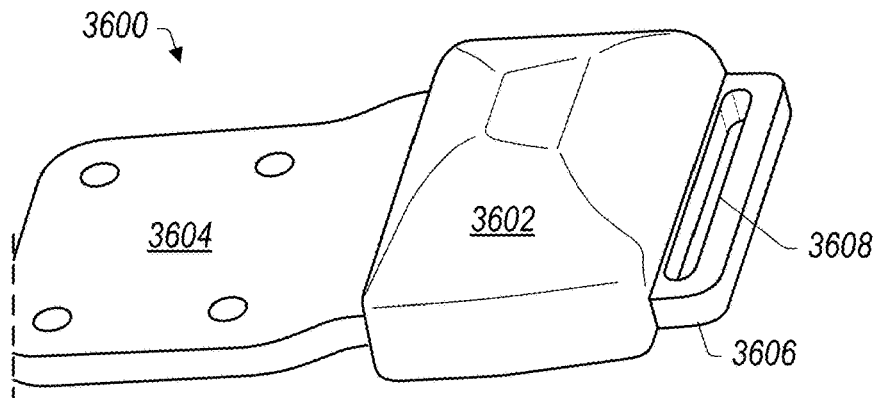

FIG. 37 depicts a representation of an embodiment of a force sensing element.

Figure 38:
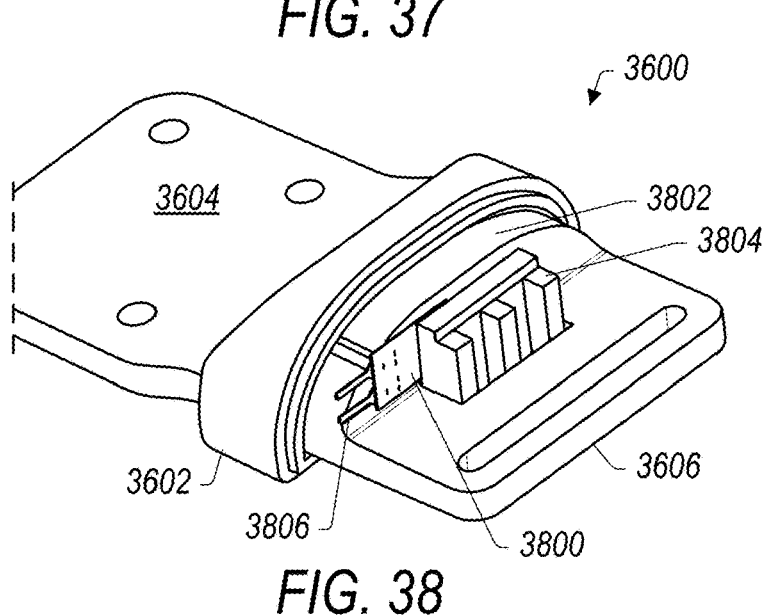

FIG. 38 depicts a representation of an embodiment of a force sensing element with a portion of a sensor cover removed.

Figure 39:
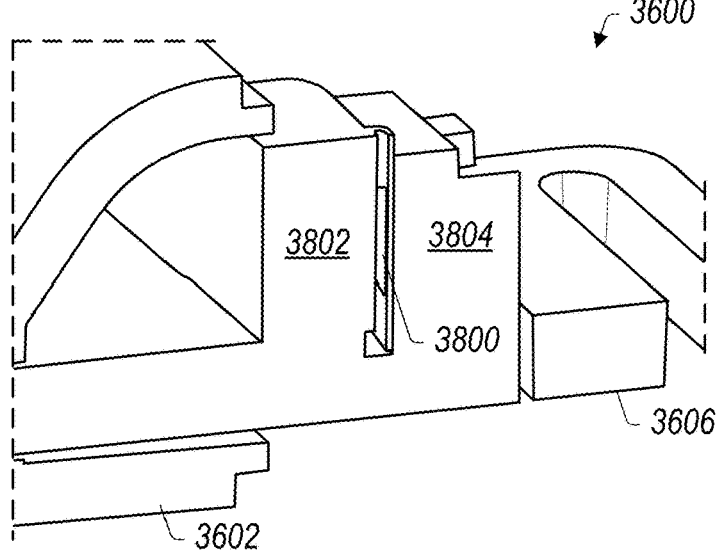

FIG. 39 depicts a cross-sectional representation of an embodiment of a force sensing element showing a sensor sandwiched between sensor body elements.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "compression" as used herein generally refers to the application of balanced inward (e.g., "pushing") forces to different points on a material or structure.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The term "engine" as used herein generally refers to a machine designed to convert one form of energy into mechanical energy (e.g., electric motors, sonic wave generators, etc.).

The phrase "oscillation force" as used herein generally refers to a vibrational force, or a vibrational wave effect or wave form.

The term "pressure" as used herein generally refers to a force applied substantially perpendicular to a surface of an object.

Portable High Frequency Physiological Oscillator

Chest physiotherapy with bronchial drainage is a known treatment for mobilization and removal of airway secretions in many types of respiratory dysfunction especially in chronic lung disease (e.g., cystic fibrosis, bronchiectasis, bronchitis, primary ciliary dyskinesia syndrome). Chest physiotherapy has been demonstrated to be effective in maintaining pulmonary function and prevention or reduction of respiratory complications in patients with chronic respiratory diseases. In some embodiments, a system and/or method may include clearing a biological airway. Biological airways may include any portion of the respiratory system including, but not limited to, trachea, bronchi, bronchioles, and alveoli.

The method may include positioning a wearable system on a subject. The method may include adjusting the wearable system such that an oscillation force is applied to at least a first zone and to at least a second zone of the subject (e.g., and possibly more zones). In some embodiments, an oscillation force may include a vibrational force, or a vibrational wave effect or wave form.

Figures 1, 2:
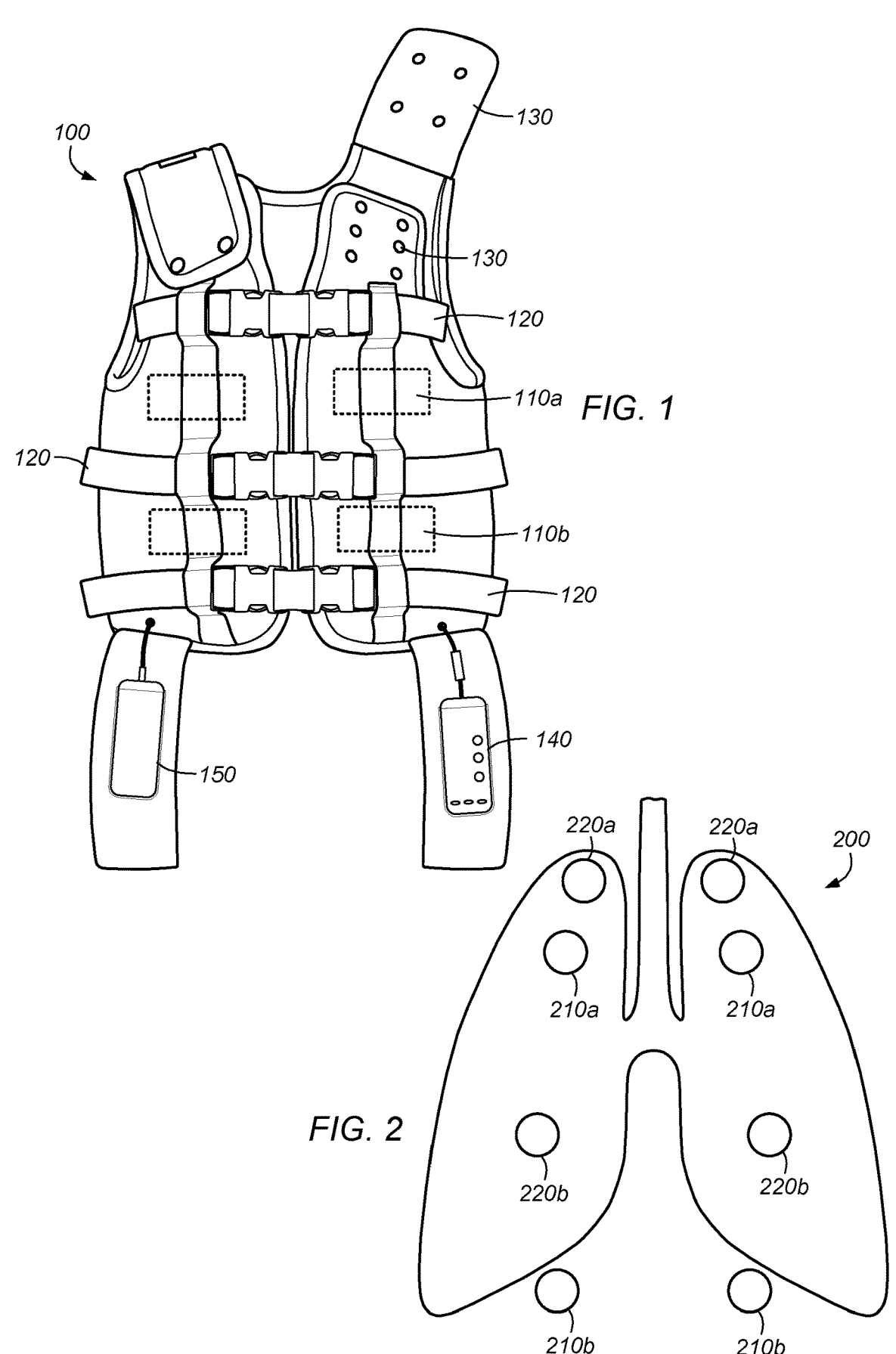
FIG. 1 depicts a front perspective view of a representation of an embodiment of a portable high frequency chest wall oscillator system.
FIG. 2 depicts a front view of a representation of an embodiment of a pair of human lungs.

FIG. 1 depicts a front perspective view of a representation of an embodiment of a portable high frequency chest wall oscillator system 100. Known HFCWO systems do not allow for a user adjusting where forces are applied to on the subject. This is problematic because although some known HFCWO systems may come in different sizes to accommodate differently sized subjects, there are far too many people of different sizes and so it is impractical to produce enough differently sized systems for all of the differently sized subjects. FIG. 2 depicts a front view of a representation of an embodiment of a pair of human lungs 200. Known HFCWO systems may typically apply forces at zones 210*a*-*b*. A system 100 may allow for adjusting where forces are applied to the subject, for example, to what are identified as at least the first zone 220*a* and the second zone 220*b*. Applying high frequency forces to zones 220 as opposed to zones 210 may allow for greater remediation of symptoms associated with certain forms of chronic lung disease.

In some embodiments, the first zone 220*a* may be proximate to and below a collarbone of the subject (e.g., as depicted in FIG. 2). FIG. 2 depicts a front view of a representation of an embodiment of a pair of human lungs 200. In some embodiments, the second zone 220*b* may be positioned below first zone and proximate to and above a bottom of a rib cage of the subject (e.g., as depicted in FIG. 2). In some embodiments, the first and/or second zone may be positioned relative to any relevant markers (e.g., one or more of the subject's physiological markers) which results in increased mobilization of secretions in an airway within the subject. The method may include applying a force (e.g., an oscillation force, a high frequency force, a pneumatic force, etc.) to the first zone and/or the second zone (e.g., and possibly additional zones) using a first engine 110*a* and a second engine 110*b* respectively. The method may include mobilizing secretions in an airway within the subject (e.g., substantially adjacent the first and/or second zone). In some embodiments, an engine may include electric motors, sonic wave generators, etc.

In some embodiments, mobilizing secretions may include generating increased airflow velocities and/or percussive or oscillation forces resulting in cough-like shear forces. In some embodiments, mobilizing secretions may include decreasing a viscosity of at least some secretions in an airway within the subject substantially adjacent the first and/or second zone. Mobilizing secretions may assist subjects to move retained secretions from smaller airways to larger airways where they may move more easily via coughing. In some embodiments, secretions may include what is generally referred to as mucus. Mucus may include water, ions, soluble mediators, inflammatory cells, and/or secreted mucins. In some embodiments, secretions may include any fluids (e.g., excessive fluids) potentially blocking subject airways.

In some embodiments, adjusting the wearable system may include adjusting fastening systems which couple the wearable system to the subject. In some embodiments, the wearable system may be adjustable at least across a chest and/or portion of a torso of a subject (e.g., as depicted in FIG. 1 using friction fittings and straps 120). In some embodiments, the wearable system may be adjustable at least across one or more shoulders of a subject (e.g., as depicted in FIG. 1). In some embodiments, the wearable system may be adjustable using one or more fasteners 130 using at least one type of fastener. In some embodiments, adjusting the wearable system may include positioning the first engine or the second engine (e.g., and possibly additional engines) relative to the first zone or the second zone (e.g., and possibly additional zones) respectively. In some embodiments, a fastener may include a plurality of snaps 130 coupling the wearable system across the shoulder of a subject (e.g., as depicted in FIG. 1) such that the engines may positioned appropriately relative to the airways of the subject. By attaching the fasteners in different combinations with one another the engines may be adjusted relative to the subject.

Figure 6:
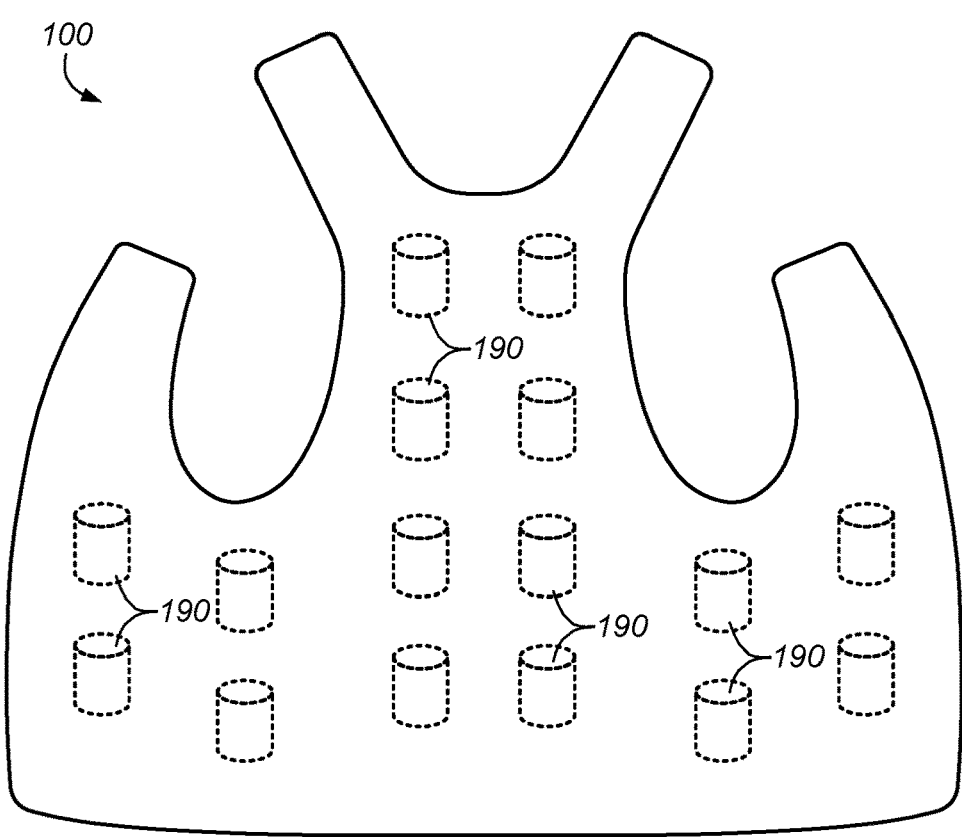
FIG. 6 depicts a front perspective view of a representation of an embodiment of a portable high frequency chest wall oscillator harness using sealable containers coupling system positioned on a subject.

In some embodiments, engines may be repositioned or adjusted relative to a subject using a system (e.g., by a doctor) which inhibits a subject from repositioning the engines once positioned. For example, a wearable garment may include a plurality of pockets or containers which engines may be positioned in and then sealed in. FIG. 6 depicts a front perspective view of a representation of an embodiment of a wearable system 100 using a plurality of sealable containers 190 coupling system used to couple the engines to the wearable system.

Figure 3:
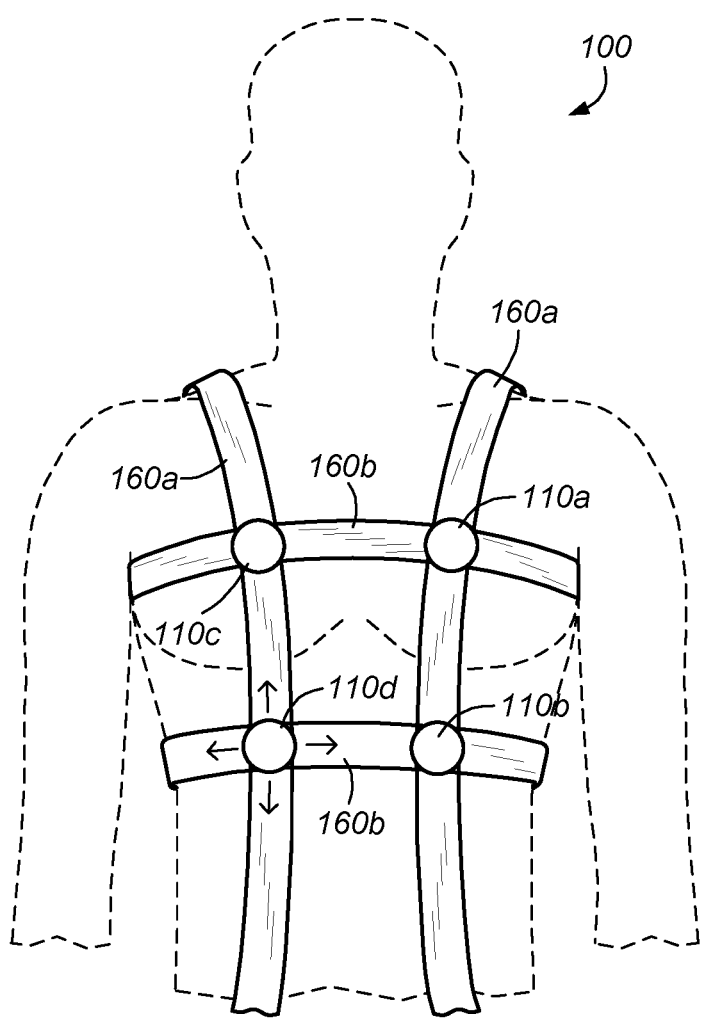
FIG. 3 depicts a front perspective view of a representation of an embodiment of a portable high frequency chest wall oscillator harness.

In some embodiments, the system may include a wearable system (e.g., as depicted in FIG. 1) which resembles a vest (e.g., coupled or directly attached at least across a front, side, and/or back). In some embodiments, the system may include a wearable system which includes a plurality of bands and/or straps 160 (e.g., as depicted in FIG. 3). FIG. 3 depicts a front perspective view of a representation of an embodiment of a portable high frequency chest wall oscillator harness 100. In some embodiments, the bands 160 (e.g., as depicted in FIG. 3) may be incorporated into a vest (e.g., as depicted in FIG. 1). The engines 110*a*-*d* may be coupled or directly attached to the bands. The engines may be coupled or directly attached to the bands such that the engines are positionable along the bands. The bands may include vertical bands 160*a* and horizontal bands 160*b*. Positionable engines may allow the engines to be positioned appropriately to provide the greatest benefit to the subject.

Figure 4A:
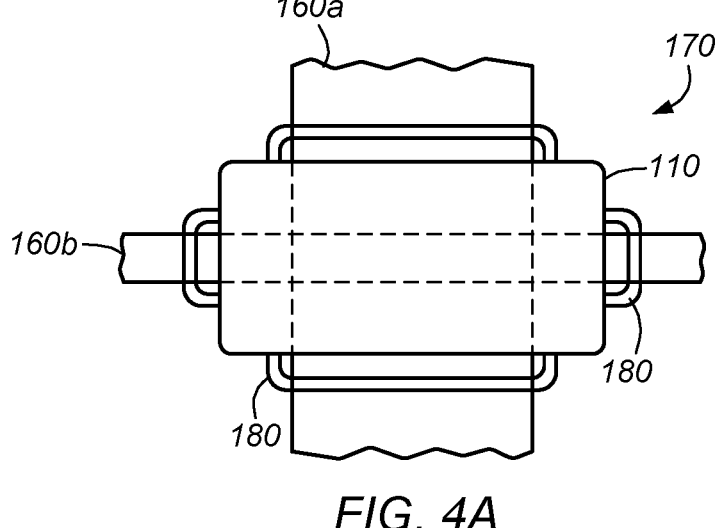
FIG. 4A depicts a front view of a representation of an embodiment of an engine coupling system.
Figure 4B:
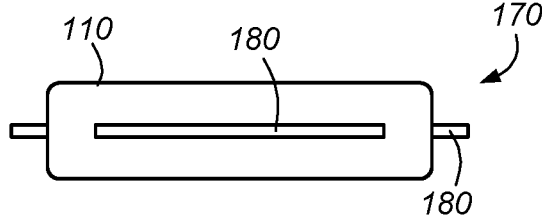
FIG. 4B depicts a side view of a representation of an embodiment of an engine coupling system.
Figure 5:
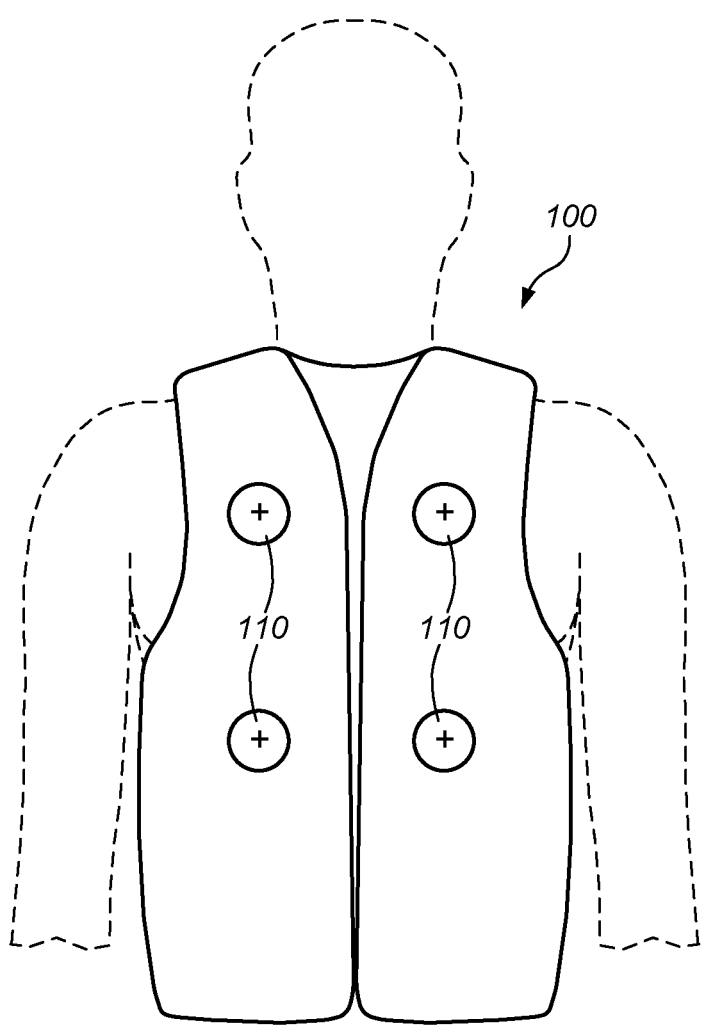
FIG. 5 depicts a front perspective view of a representation of an embodiment of a portable high frequency chest wall oscillator harness using a hook and loop coupling system positioned on a subject.

The engines may be positionally coupled or directly attached to the bands and/or system using a number of means known such that the engines may be repositioned during use as appropriate for individual subjects. In some embodiments, a hook and loop system may be used to couple the engines to a wearable system such that the engines are repositionable. FIG. 5 depicts a front perspective view of a representation of an embodiment of a wearable system 100 using a hook and loop system to couple engines 100 to the system. In some embodiments, a cleat 170 may be used to couple the engine to one or more of the bands. FIG. 4A depicts a front view of a representation of an embodiment of an engine coupling system 170. FIG. 4B depicts a side view of a representation of an embodiment of an engine coupling system 170. The cleat may include a locking mechanism 180 which once locked may inhibit movement of the cleat along the band(s). In some embodiments, a coupling mechanism may couple a horizontal band 160*b* to a vertical band 160a such that engines are repositioned relative to the subject by repositioning the bands relative to one another. The bands may include coupling mechanisms as depicted in FIG. 1 in order to couple the bands to a subject. The lengths of the bands may be adjustable as well in order to fit the bands to the subject.

In some embodiments, the wearable system 100 may include multiple engines 110 (e.g., eight or more engines). The system may include at least four engines 110, at least six engines 110, or at least eight engines 110 (e.g., as depicted in FIG. 1, although only the front four are depicted, the remaining four are on the back of the system 100). In some embodiments, the system may include eight engines. In some embodiments, the method may include adjusting the wearable system comprises positioning a third engine or a fourth engine relative to the first zone or the second zone respectively on an opposing side of the subject opposite of the side of the first and the second engine.

In some embodiments, the system 100 may include a control unit 140. The method may include activating at least the first engine using the control unit 140. The control unit may control activation/deactivation/adjustment of all of the engines of the system 100. In some embodiments, the control unit 140 may be couplable to the system 100 (e.g., using a flap of material which may be used to cover and protect the control unit as depicted in FIG. 1). The control unit 140 may be directly wired to the engines 110 and/or may be wirelessly coupled or directly attached to the engines. The control unit may use any number of known input methods (e.g., including touchpad). The control unit may be digital or analog. In some embodiments, the control unit may adjust one or more settings of the engines. The control unit may adjust the oscillation force output by the engine. The control unit may adjust an amplitude of the oscillation force output by the engine. The control unit may adjust a frequency of the oscillation force output by the engine. In some embodiments, engine parameters may be adjusted via software (e.g., a phone app) remotely (e.g., Wi-Fi, Bluetooth, etc.). In some embodiments, the engines 110 may include a frequency range from 5 Hz to 20 Hz. In some embodiments, the intensity levels dictate the frequency which generally runs at 5 Hz for the lowest setting, 13 Hz for the medium setting and 20 Hz for the highest setting.

In some embodiments, a method may include modifying the treatment parameters (e.g., amplitude, frequency, and time for each engine). Each engine may be programmed, using physical hardware control unit or software to run a custom cycle. This programming may be performed by the subject. In addition, the system may provide a physician or caregiver with the ability to prescribe a defined treatment and to inhibit the user from modifying the treatment settings (e.g., lock-out feature w/password, pin code, etc.).

In some embodiments, the method and/or system may adaptively modify the treatment protocol based on subject and/or physician feedback. For example, a subject enters mucus secretion levels after each treatment and the system adaptively optimizes the treatment settings over time.

In some embodiments, the method and/or system may monitor compliance for each subject, including parameters run, time of treatment, information. For example, the system could monitor (in real-time) the treatment time of day and any subject feedback. This could be accomplished through hardware or software (e.g., a web-based subject/physician portal which links w/Bluetooth to each vest). The information may be provided to the subject, physician, insurance company or other third-party.

In some embodiments, the system 100 may include at least one battery 150. The method may include powering at least the first engine 110a using one or more batteries 150 coupled or directly attached to the wearable system. In some embodiments, a battery 150 may include a rechargeable battery and/or a disposable battery. The battery 150 may include two or more batteries. The batteries 150 may be easily swapped out whether rechargeable or disposable. The battery 150 may be coupled or directly attached to the system 100 (e.g., using a flap of material which may be used to cover and protect the battery as depicted in FIG. 1). The system may include an adapter such that, when necessary, the system may be coupled or directly attached to an electrical outlet (e.g., through an electrical adapter if necessary). The system 100 may be powered using AC or DC power sources such that the system may be powered using virtually any known power source currently available.

In some embodiments, the system may be self-contained. The system may be self-contained such that a subject may wear the system 100 and move freely and in a substantially unrestricted manner. The system may be self-contained such that a subject may wear the system 100 while functioning and not physically connected to any external devices (e.g., air pumps).

Upper Chest Portable High Frequency Physiological Oscillator

In some embodiments, a system and/or method may include clearing a biological airway(s). As discussed though even wearable systems as described herein may not be sufficient to assist a subject in fully clearing the subject's biological airway. In some instances, secretions may be moved out of the lungs but not high enough into the major bronchial tubes and/or trachea such that a subject may evacuate the secretions from the subject (especially with the reduced air capacity of the subject who need to employ systems as described herein). It would be beneficial to have a system which works alone or in combination with the vest/harnesses described herein to further move a subject's secretions out of the subject's airways.

In some embodiments, the method may include positioning a wearable system around a subject's neck. The wearable system may be coupled or directly attached to another wearable garment such that the wearable system is positioned substantially around at least a portion of the subject's neck. The method may include adjusting the wearable system such that an oscillation force is applied to at least an upper first zone of the subject. The upper first zone may be proximate to a collarbone of the subject and proximate to a juxtaposition of the subject's bronchial tubes and trachea on a first side of the subject. The method may include applying the oscillation force to at least upper first zone using an upper first engine. The method may include mobilizing at least some secretions in an airway within the subject substantially adjacent the first zone so that it may be expelled by the subject.

Figure 7:
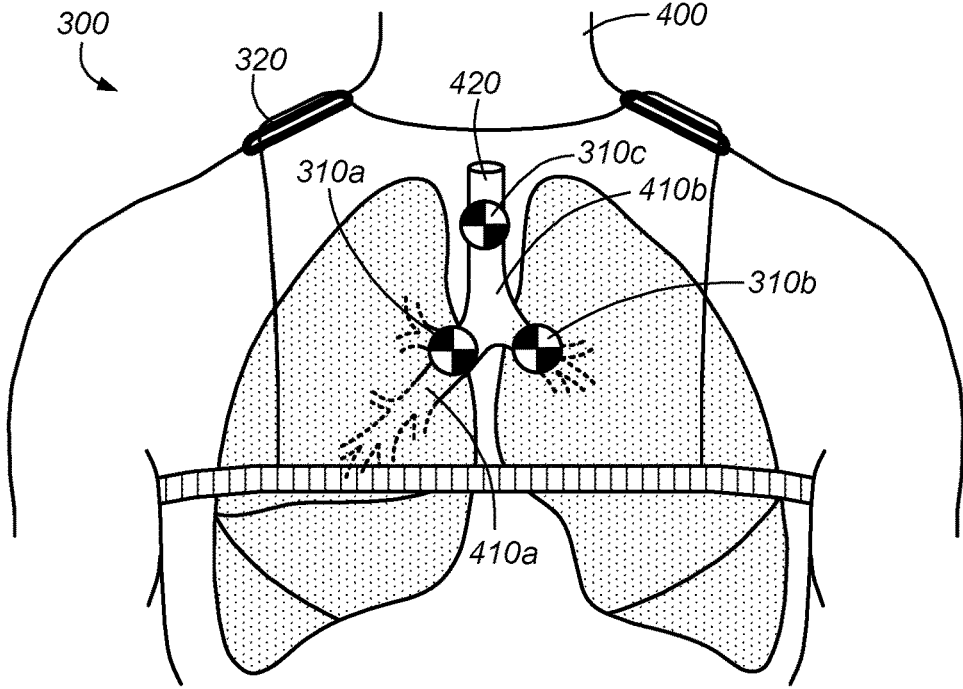
FIG. 7 depicts a representation of an embodiment of a portable high frequency physiological oscillator harness positioned around a subject's neck.

FIG. 7 depicts a representation of an embodiment of a portable high frequency physiological oscillator harness 300 positioned around a subject's neck 400. In some embodiments, the upper first engine 310 may include one or more engines. The engines may be separately powered and/or controlled. The upper first engine may include at least three engines 310a-c. In some embodiments, a first 310a of the three engines may be positioned proximate a first bronchial tube 410a extending from the juxtaposition. A second 310b of the three engines may be positioned proximate a second bronchial tube 410b extending from the juxtaposition. A third 310c of the three engines may be positioned proximate the trachea 420. Positioning at least one (e.g., three) engine in such a fashion may assist a subject in clearing secretions out of the subject's airways, especially when used in combination with the vest/harness described herein. The vest/harness described herein may assist in moving secretions from a subject's airways in the lungs up into the at least major bronchial passages adjacent/in the upper first zone wherein the wearable system may further move the subject's secretions out of the subject.

In some embodiments, the method may include adjusting the wearable system such that the oscillation force is applied to at least an upper second zone of the subject. The upper second zone may be proximate to the collarbone of the subject and proximate to the juxtaposition of the subject's bronchial tubes and trachea. The upper second zone may be positioned on a second side of the subject, wherein the second side is on an opposing side of the subject from the first side. The method may include applying the oscillation force to the at least upper second zone using an upper second engine. The upper second engine may include at least one (e.g., three) engines.

Figure 8:
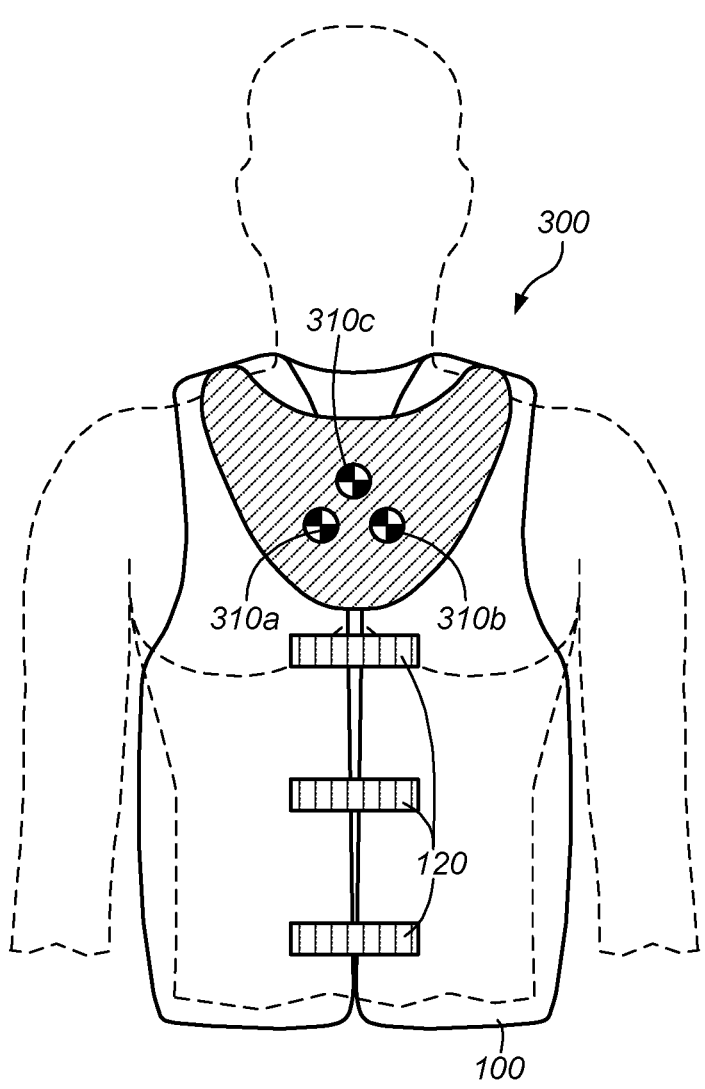
FIG. 8 depicts a representation of an embodiment of a portable high frequency physiological oscillator harness positioned around a subject's neck in combination with portable high frequency chest wall oscillator vest.

In some embodiments, the wearable system 300 may include adjustable fastening systems 320 which couple the wearable system to the subject. Adjustable fastening systems may include snaps buckles, Velcro, etc. FIG. 8 depicts a representation of an embodiment of a portable high frequency physiological oscillator harness positioned around a subject's neck in combination with portable high frequency chest wall oscillator vest. The wearable system 300 may be used in combination with other systems which function to mobilize internal lung secretions. The wearable system 300 may be used without any other systems in order to mobilize internal lung secretions such that the secretions are expelled out of the subject.

In some embodiments, the system 300 may include a control unit 140 (e.g., a control unit of the system 300 may function independently of other possible control units, a control unit of the system 300 may be electrically coupled or directly attached to the control unit of the vest when used in combination with the vest, or the system 300 may not include an independent control unit and the system 300 may be coupled or directly attached into a control unit of a wearable system 100). The method may include activating at least the upper first engine using the control unit 140. The control unit may control activation/deactivation/adjustment of all of the engines of the system 300. In some embodiments, the control unit 140 may be couplable to the system 300 (e.g., using a flap of material which may be used to cover and protect the control unit). The control unit 140 may be directly wired to the engines 310 and/or may be wirelessly coupled or directly attached to the engines. The control unit may use any number of known input methods (e.g., including touchpad). The control unit may be digital or analog. In some embodiments, the control unit may adjust one or more settings of the engines. The control unit may adjust the oscillation force output by the engine. The control unit may adjust an amplitude of the oscillation force output by the engine. The control unit may adjust a frequency of the oscillation force output by the engine. In some embodiments, engine parameters may be adjusted via software (e.g., a phone app) remotely (e.g., Wi-Fi, Bluetooth, etc.). In some embodiments, the engines 310 may include a frequency range from 5 Hz to 20 Hz. In some embodiments, the intensity levels dictate the frequency which generally runs at 5 Hz for the lowest setting, 13 Hz for the medium setting and 20 Hz for the highest setting.

In some embodiments, a method may include modifying the treatment parameters (e.g., amplitude, frequency, and time for each engine). Each engine may be programmed, using physical hardware control unit or software to run a custom cycle. This programming may be performed by the subject. In addition, the system may provide a physician or caregiver with the ability to prescribe a defined treatment and to inhibit the user from modifying the treatment settings (e.g., lock-out feature w/password, pin code, etc.).

In some embodiments, the method and/or system may adaptively modify the treatment protocol based on subject and/or physician feedback. For example, a subject enters mucus secretion levels after each treatment and the system adaptively optimizes the treatment settings over time.

In some embodiments, the method and/or system may monitor compliance information. For example, the system could monitor (in real-time) the treatment for each subject, including parameters run, time of treatment, time of day and any subject feedback. This could be accomplished through hardware or software (e.g., a web-based subject/physician portal which links w/ Bluetooth to each vest). The information may be provided to the subject, physician, insurance company or other third-party.

In some embodiments, the system 300 may include at least one battery 150 (e.g., a battery of the system 300 may function independently of other possible batteries, a battery of the system 300 may be electrically coupled or directly attached to the battery of the vest when used in combination with the vest, or the system 300 may not include an independent battery and the system 300 may be coupled or directly attached into a battery of a wearable system 100). The method may include powering at least the upper first engines 310 using one or more batteries 150 coupled or directly attached to the wearable system. In some embodiments, a battery 150 may include a rechargeable battery and/or a disposable battery. The battery 150 may include two or more batteries. The batteries 150 may be easily swapped out whether rechargeable or disposable. The battery 150 may be coupled or directly attached to the system 300 (e.g., using a flap of material which may be used to cover and protect the battery). The system may include an adapter such that, when necessary, the system may be coupled or directly attached to an electrical outlet (e.g., through an electrical adapter if necessary). The system 300 may be powered using AC or DC power sources such that the system may be powered using virtually any known power source currently available.

In some embodiments, the system may be self-contained. The system may be self-contained such that a subject may wear the system 300 and move freely and in a substantially unrestricted manner. The system may be self-contained such that a subject may wear the system 300 while functioning and not physically connected to any external devices (e.g., air pumps).

Positionable Oscillating Motor Array with Potentially Disposable and/or Recyclable Portions In some embodiments, it is advantageous to form a wearable system with one or more disposable portions. There are many advantages to having a wearable system formed from at least in part disposable portions including facilitating use of the wearable system in different environments (e.g., hospitals, clinics, etc.). Professional healthcare environments are required to constantly be vigilant regarding sanitation and cross contamination between patients. To this end medical equipment must be sanitized before being used again. However, sanitizing equipment is typically time consuming and/or expensive. As such much of the equipment used in healthcare environments which comes into direct contact with subjects is disposable (or covered by disposable sheaths). It is typically much easier and/or less expensive to throw away equipment which comes into contact with subjects as opposed to cleaning the equipment.

The method may include positioning a wearable system on a subject. The method may include adjusting the wearable system such that an oscillation force is applied to at least a first zone and to at least a second zone of the subject (e.g., and possibly more zones). In some embodiments, the oscillation force may be infinitely adjustable relative to the subject. Having an infinitely adjustable oscillation force (e.g., infinitely positionable engines) may allow customizable positioning of the oscillation force as required by the subject (e.g., as prescribed by a care giver (e.g., doctor, nurse, etc.).

In some embodiments, mobilizing secretions may include generating increased airflow velocities and/or percussive or oscillation forces resulting in cough-like shear forces. In some embodiments, mobilizing secretions may include decreasing a viscosity of at least some secretions in an airway within the subject substantially adjacent the first and/or second zone. Mobilizing secretions may assist subjects to move retained secretions from smaller airways to larger airways where they may move more easily via coughing. In some embodiments, secretions may include what is generally referred to as mucus. Mucus may include water, ions, soluble mediators, inflammatory cells, and/or secreted mucins. In some embodiments, secretions may include any fluids (e.g., excessive fluids) potentially blocking subject airways.

Figure 9A:
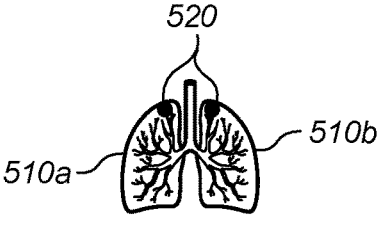
FIGS. 9A-J depict representations of different areas of a subject's lungs which may require treatment using herein described systems and methods.
Figure 9A:
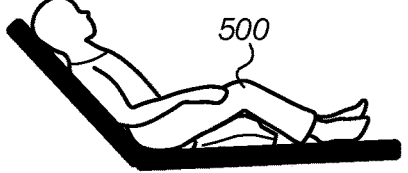
Figure 9B:
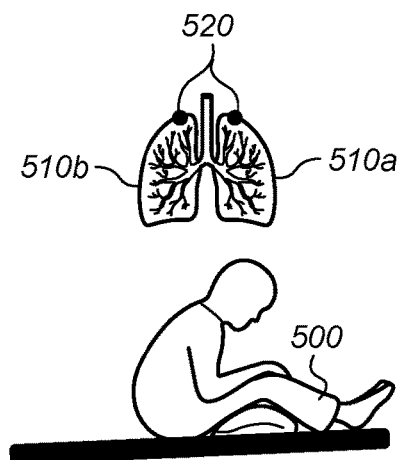
Figure 9C:
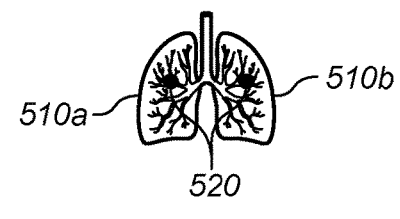
Figure 9C:
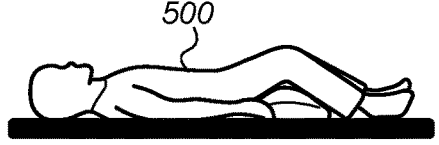
Figure 9D:
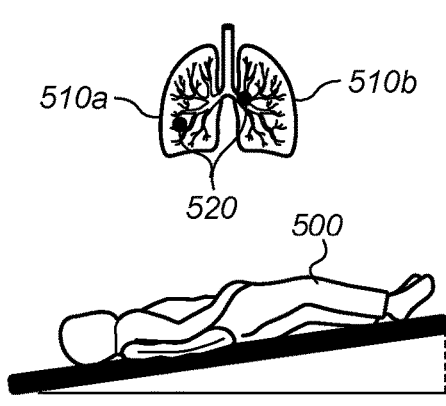
Figure 9E:
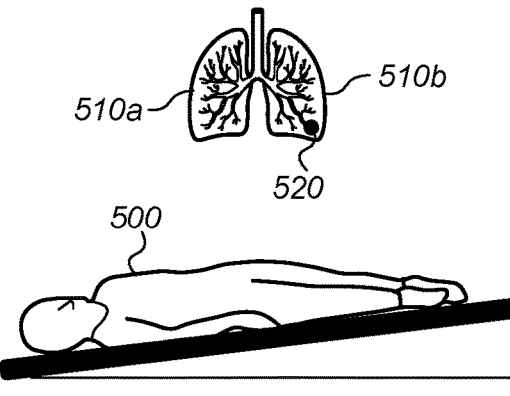
Figure 9F:
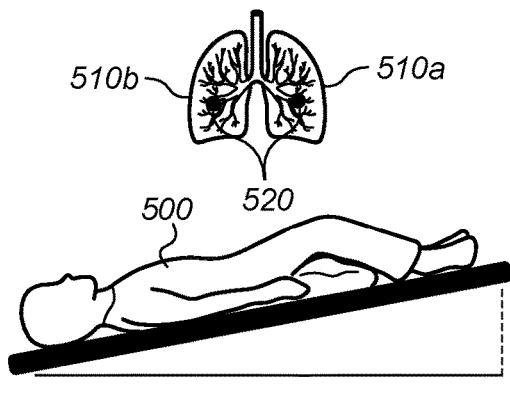
Figure 9G:
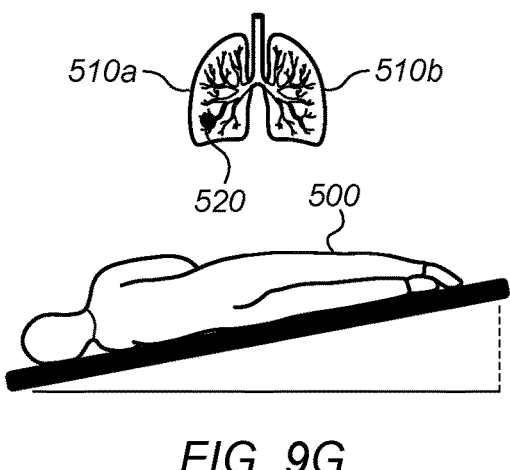
Figure 9H:
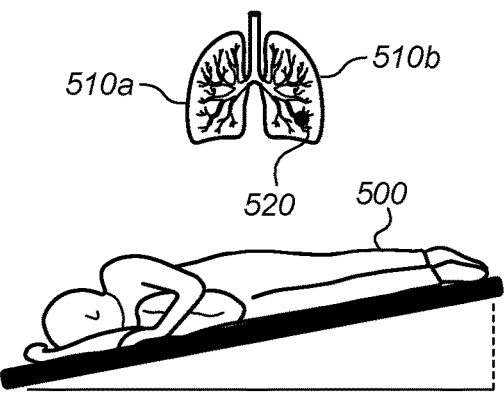
Figure 9I:
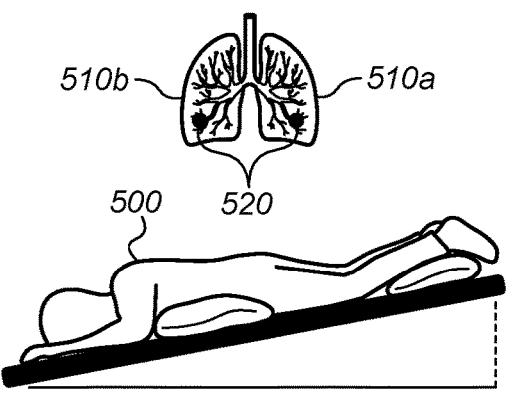
Figure 9J:
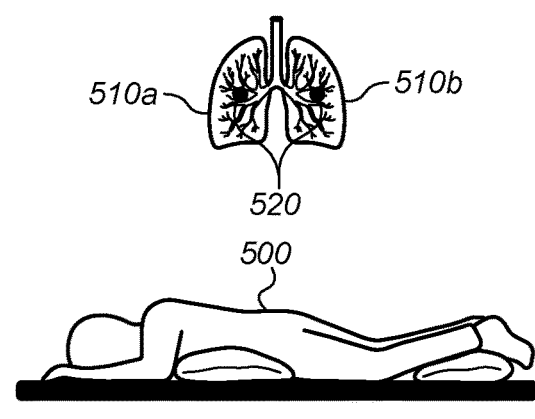

Depending upon the subject's specific condition one or more engines may be positioned accordingly (e.g., around the area of trouble for the subject which require treatment). FIGS. 9A-J depict representations of different areas of a subject's lungs 510a-b which may require treatment using herein described systems and methods. FIGS. 9A-J depict representations of right lung 510a and left lung 510b of subject 500. Zones 520 of lungs 510 are examples of areas in a subject which may need treatment and/or wherein treatment may be applied as prescribed by a physician for treatment. FIGS. 9A-J depict representations of subject 500 positioned for extracting fluids from lungs 510 using known percussion methods. In some embodiments, positioning the subject 500, as depicted in FIGS. 9A-J for example, may be used in combination with the systems and methods described herein. In some embodiments, any special positioning of the subject may not be necessary and/or used in combination with the systems and methods described herein. FIG. 9A depicts subject 500 positioning and/or zones 520 for treating (e.g., applying oscillation forces using systems and methods described herein) respiratory afflictions affecting the left and right anterior apical portions of lungs 510. FIG. 9B depicts subject 500 positioning and/or zones 520 for treating (e.g., applying oscillation forces using systems and methods described herein) respiratory afflictions affecting the left and right posterior apical portions of lungs 510. FIG. 9C depicts subject 500 positioning and/or zones 520 for treating (e.g., applying oscillation forces using systems and methods described herein) respiratory afflictions affecting the left and right anterior segments of lungs 510. FIG. 9D depicts subject 500 positioning and/or zones 520 for treating (e.g., applying oscillation forces using systems and methods described herein) respiratory afflictions affecting the right middle lobe portion of lung 510. FIG. 9E depicts subject 500 positioning and/or zones 520 for treating (e.g., applying oscillation forces using systems and methods described herein) respiratory afflictions affecting the left singular portion of lung 510. FIG. 9F depicts subject 500 positioning and/or zones 520 for treating (e.g., applying oscillation forces using systems and methods described herein) respiratory afflictions affecting the left and right anterior basil portions of lungs 510. FIG. 9G depicts subject 500 positioning and/or zones 520 for treating (e.g., applying oscillation forces using systems and methods described herein) respiratory afflictions affecting the right lateral basal portion of lung 510. FIG. 9H depicts subject 500 positioning and/or zones 520 for treating (e.g., applying oscillation forces using systems and methods described herein) respiratory afflictions affecting the left lateral basal portion of lung 510. FIG. 9I depicts subject 500 positioning and/or zones 520 for treating (e.g., applying oscillation forces using systems and methods described herein) respiratory afflictions affecting the left and right posterior basal portions of lungs 510. FIG. 9J depicts subject 500 positioning and/or zones 520 for treating (e.g., applying oscillation forces using systems and methods described herein) respiratory afflictions affecting the left and right superior basal portions of lungs 510. FIGS. 9A-J depict representations of how systems described herein may be used as examples of prescriptive positioning of engines by a caregiver.

Figure 10:
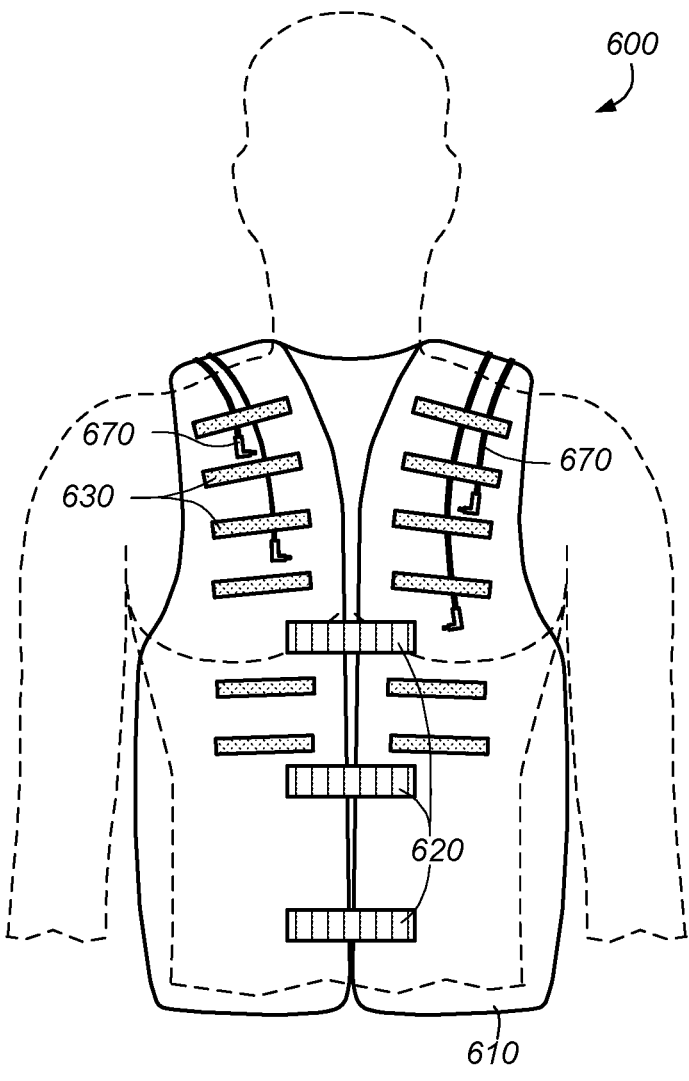
FIG. 10 depicts a front view of a representation of an embodiment of a portable high frequency chest wall oscillator inner harness positioned on a subject.

FIG. 10 depicts a front perspective view of a representation of an embodiment of a portable high frequency chest wall inner harness 610 of an oscillator system 600. Known HFCWO systems do not allow for a user adjusting where forces are applied to on the subject. This is problematic because although some known HFCWO systems may come in different sizes to accommodate differently sized subjects, there are far too many people of different sizes and so it is impractical to produce enough differently sized systems for all of the differently sized subjects. A system 600 which allows for adjustment and/or positioning of one or more engines and/or one or more groups of engines may allow for prescriptive oscillation or prescriptive positioning of engines by a caregiver. For example, a caregiver may employ means to visualize (e.g., x-rays) secretions accumulating in the lungs of a subject and then position engines appropriately around any areas where secretions are accumulating. In some embodiments, engines may not only be simply placed adjacent treatment areas but also may be positioned adjacent to areas adjacent to the treatment area to assist in flushing out secretions from the subject (e.g., pushing the secretions outside of the subject). In some embodiments, engines may be positioned in a serpentine pattern on a subject using systems described herein to create what may be described as a wave effect of oscillation forces.

In some embodiments, a caregiver may prescribe not only the position of the engines but also the frequency of one or more of the engines. The pulse or the beat frequency of one or more of the engines may be adjusted based upon a prescribed frequency. In some embodiments, a caregiver may prescribe or program one or more or all of the engines to turn on or off.

FIG. 10 depicts a front perspective view of a representation of an embodiment of a portable high frequency chest wall inner (or first) harness 610 of an oscillator system 600. In some embodiments, inner harness 610 may be sold in multiple sizes (e.g., 3 or more sizes). The inner harness may be sold in 3 sizes (e.g., child size, small adult size, large adult size). In some embodiments, an inner harness may be custom made or sized for a subject. In some embodiments, the inner harness may be formed from a flexible, a pliable or non-rigid material (e.g., as depicted in FIGS. 10-17 and 18-25). A pliable material may allow the inner harness to fit a wider range of differently physically sized subjects. The flexible material may allow the inner harness to bunch up around a slighter framed subject once cinched up. As such an inner wearable system may initially hang loosely in some embodiments.

Figure 24:
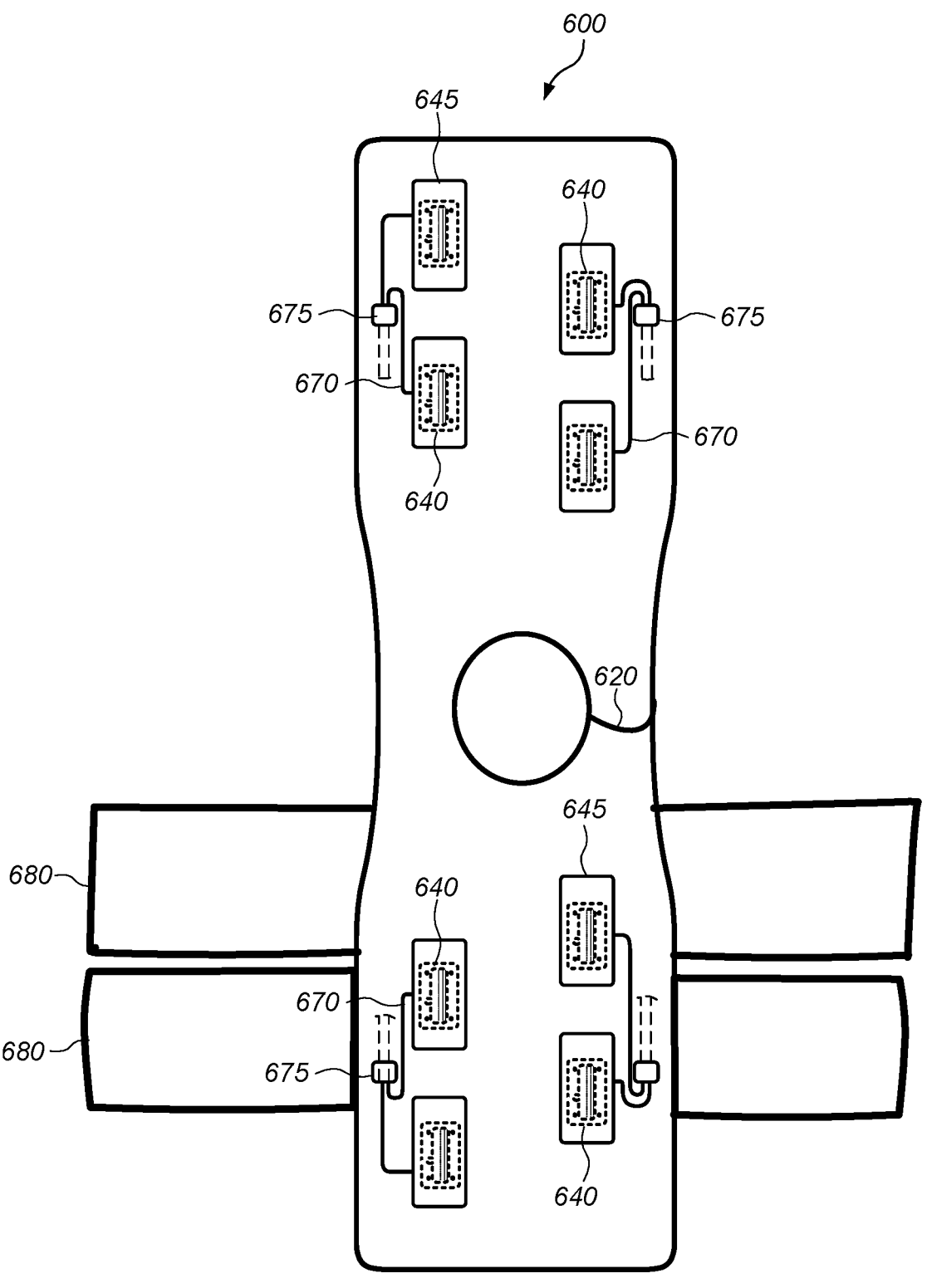
FIG. 24 depicts a front view of a representation of an embodiment of a portable high frequency chest wall oscillator inner harness including secured fasteners as well as two inactivated outer harnesses positioned on a subject.
Figure 25:
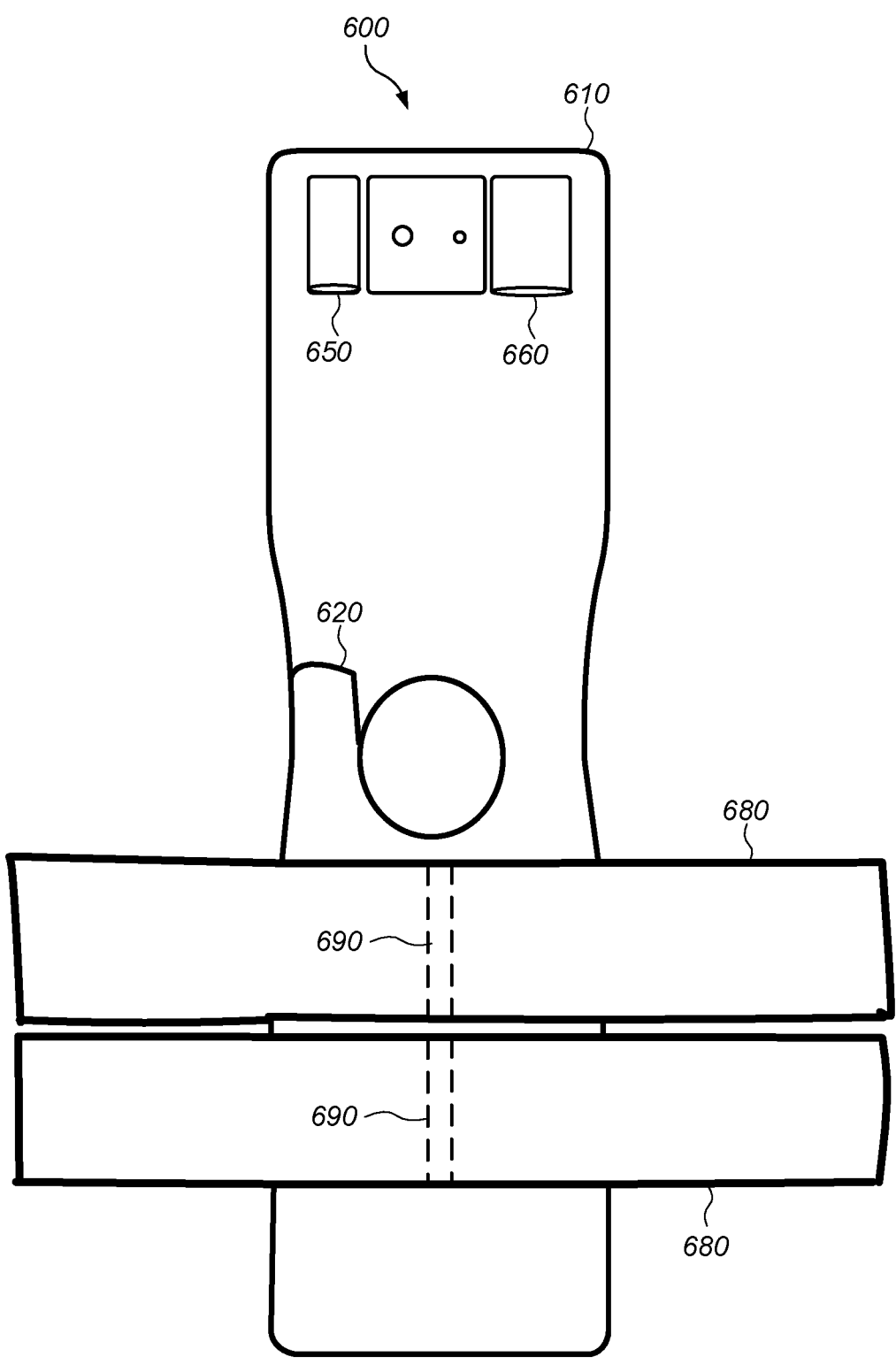
FIG. 25 depicts a front view of a representation of an embodiment of a portable high frequency chest wall oscillator inner harness including secured fasteners as well as two activated outer harnesses positioned on a subject.

In some embodiments, adjusting the wearable system inner harness may include adjusting fastening systems which couple the wearable system to the subject. In some embodiments, the wearable system may be adjustable at least across a chest and/or portion of a torso of a subject (e.g., as depicted in FIGS. 10, 10-17 and 18-23 using friction fittings and straps 620). In some embodiments, the wearable system may be adjustable at least across one or more shoulders of a subject (e.g., as depicted in FIGS. 1, 10-17 and 18-23) or one or more sides of a chest of a subject or a coupling system in a front of a subject (e.g., using zippers or lacing). In some embodiments, the wearable system may be adjustable using one or more fasteners. In some embodiments, the inner harness may include few or no size adjusting fasteners (e.g., as depicted in FIGS. 24-25).

In some embodiments, the inner harness may include a positioning system 630. The positioning system 630 may include a coupling method including, for example, a hook and loop coupling system which allows for positioning and coupling one or more portions of the oscillator system 600 to the inner harness. In some embodiments, a coupling method may include straps or pockets (e.g., as depicted in FIG. 6) used to position engines or other portions of the oscillator system 600.

In some embodiments, engines may be repositioned or adjusted relative to a subject using a system (e.g., by a doctor) which inhibits a subject from repositioning the engines once positioned.

Figure 11:
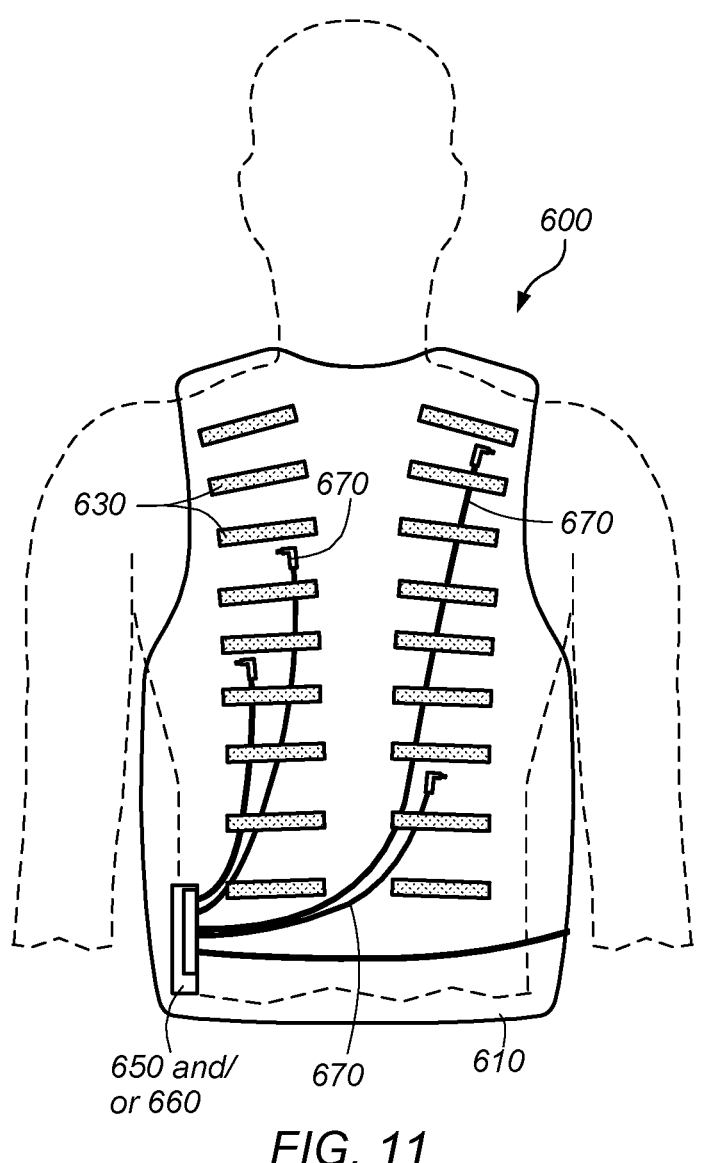
FIG. 11 depicts a rear view of a representation of an embodiment of a portable high frequency chest wall oscillator inner harness positioned on a subject.

The engines may be positionally coupled or directly attached to the bands and/or system using a number of means known such that the engines may be repositioned during use as appropriate for individual subjects. In some embodiments, a hook and loop system may be used to couple the engines to a wearable system such that the engines are repositionable. FIGS. 10-11 depict a front view and a rear view respectively of a representation of an embodiment of a portable high frequency chest wall oscillator inner harness 610 positioned on a subject. The embodiment depicted in FIGS. 10-11 includes positioning system 630 wherein the positioning system includes a plurality of hook and loop strips 630 for coupling portions of the oscillating system (e.g., engines 640, controller 650, battery 660, etc.) to the inner harness. The strips 630 depicted are just an example of a pattern of how the strips may be distributed on the harness. Specifically, the strips may be positioned on the inner harness to allow positioning engines around the treatment areas as for example as depicted in FIGS. 9A-J.

Figure 12:
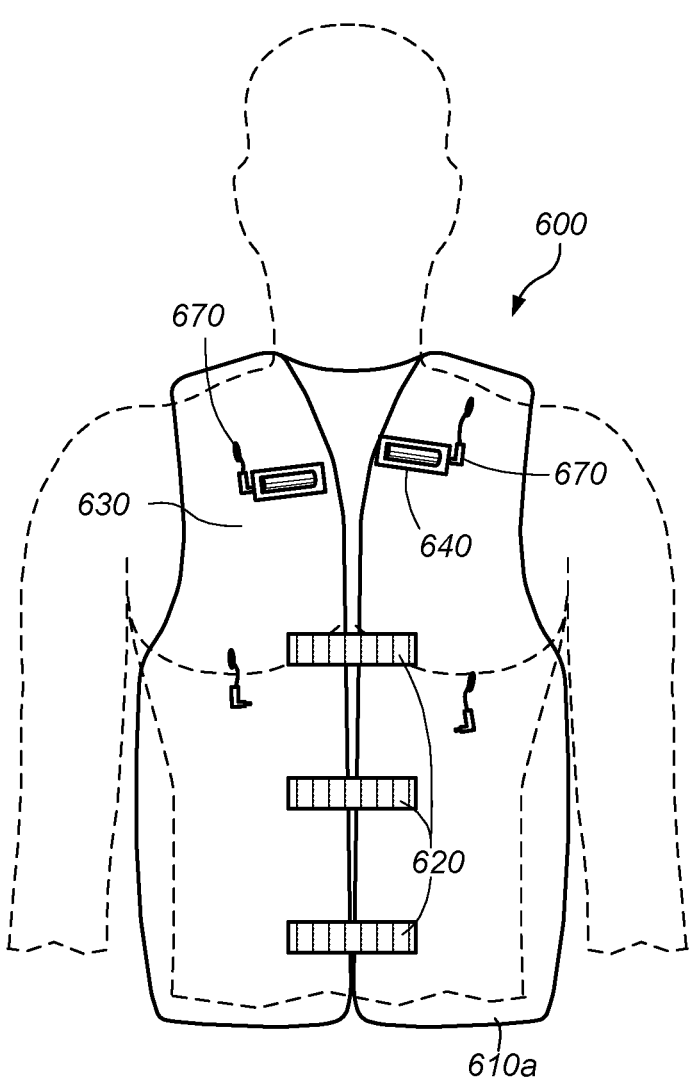
FIG. 12 depicts a front view of a representation of an embodiment of a portable high frequency chest wall oscillator inner harness positioned on a subject.
Figure 13:
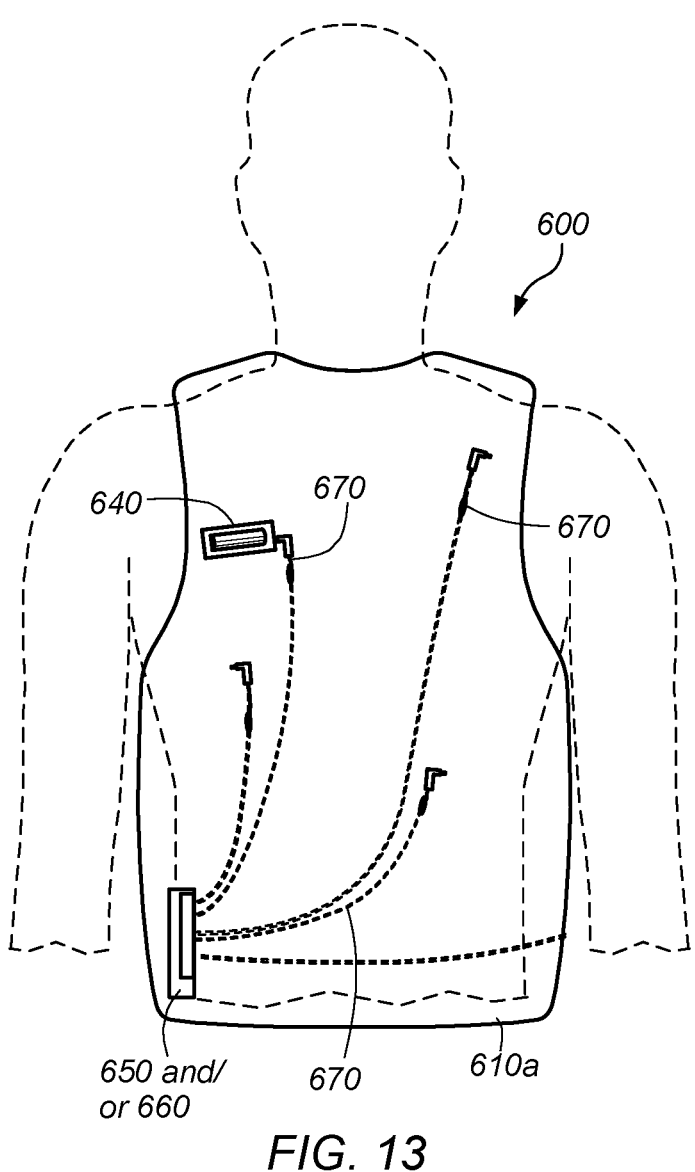
FIG. 13 depicts a rear view of a representation of an embodiment of a portable high frequency chest wall oscillator inner harness positioned on a subject.
Figure 14:
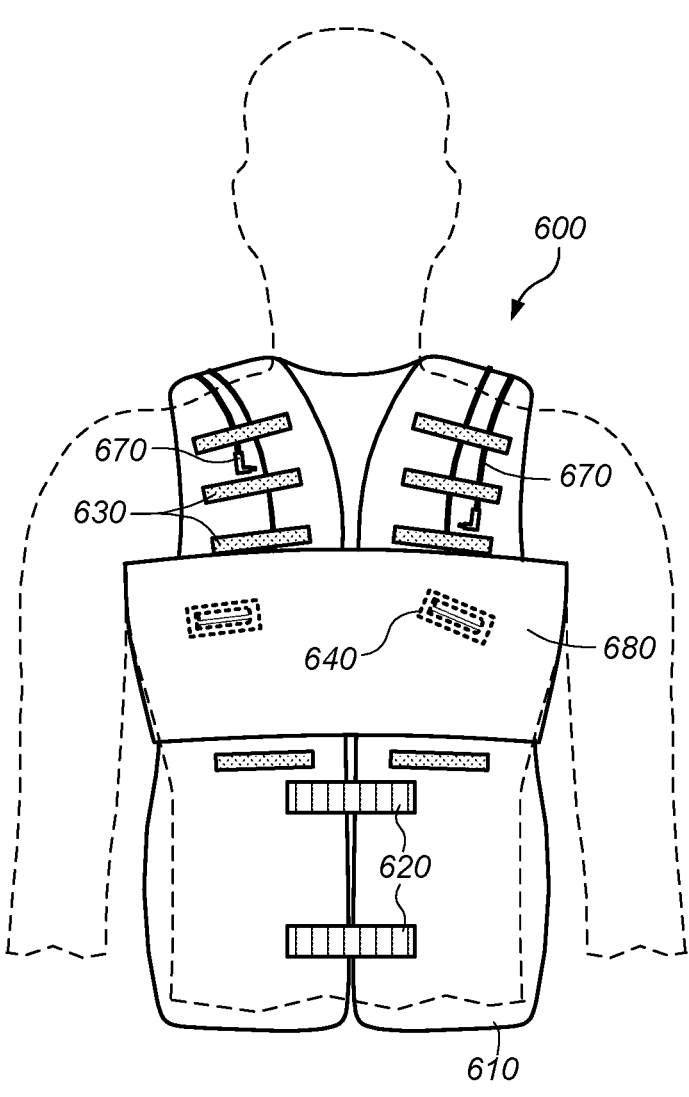
FIG. 14 depicts a front view of a representation of an embodiment of a portable high frequency chest wall oscillator inner harness and an outer harness positioned on a subject.
Figure 15:
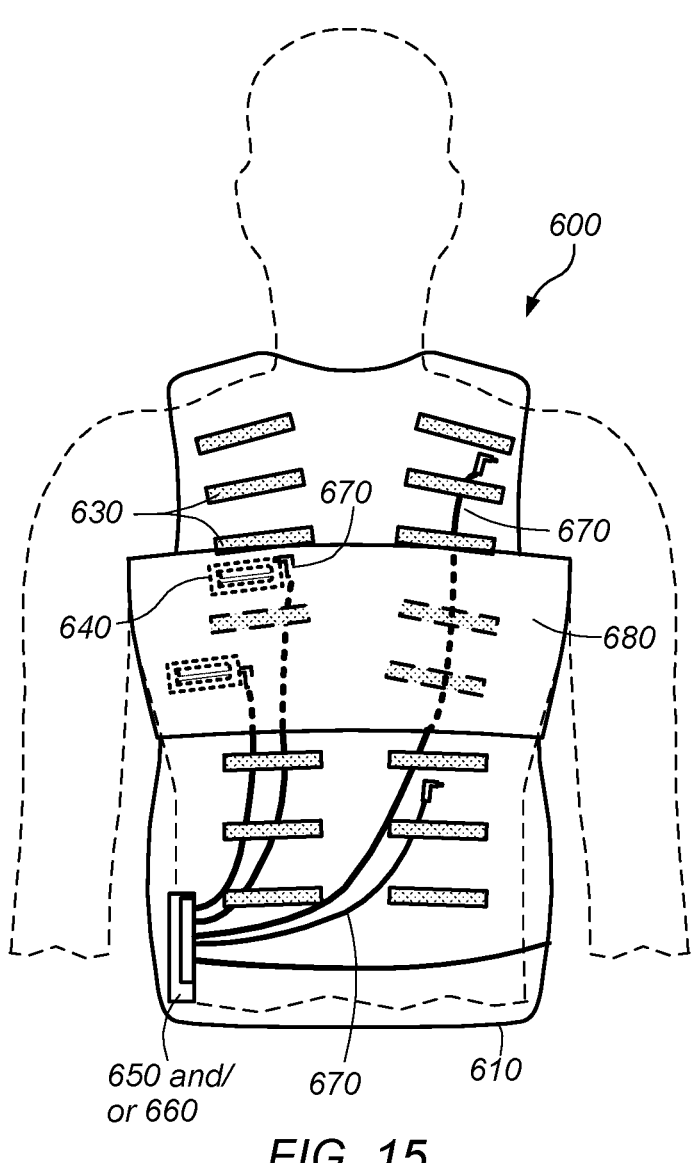
FIG. 15 depicts a rear view of a representation of an embodiment of a portable high frequency chest wall oscillator inner harness and an outer harness positioned on a subject.
Figure 16:
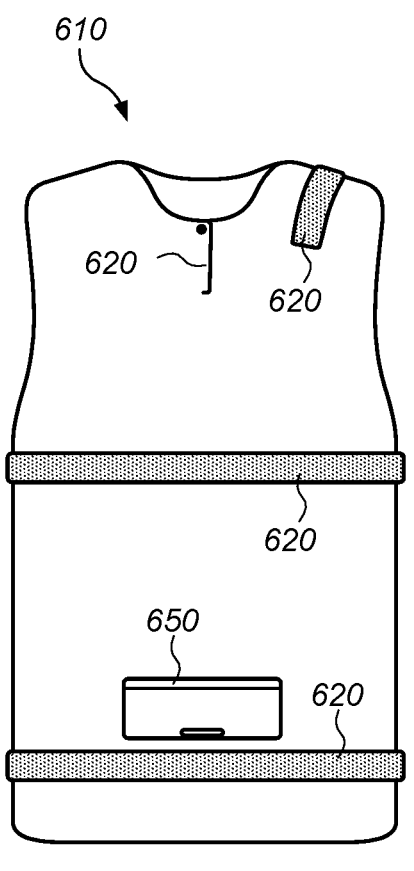
FIG. 16 depicts a front view of a representation of an embodiment of a portable high frequency chest wall oscillator inner harness.
Figure 17:
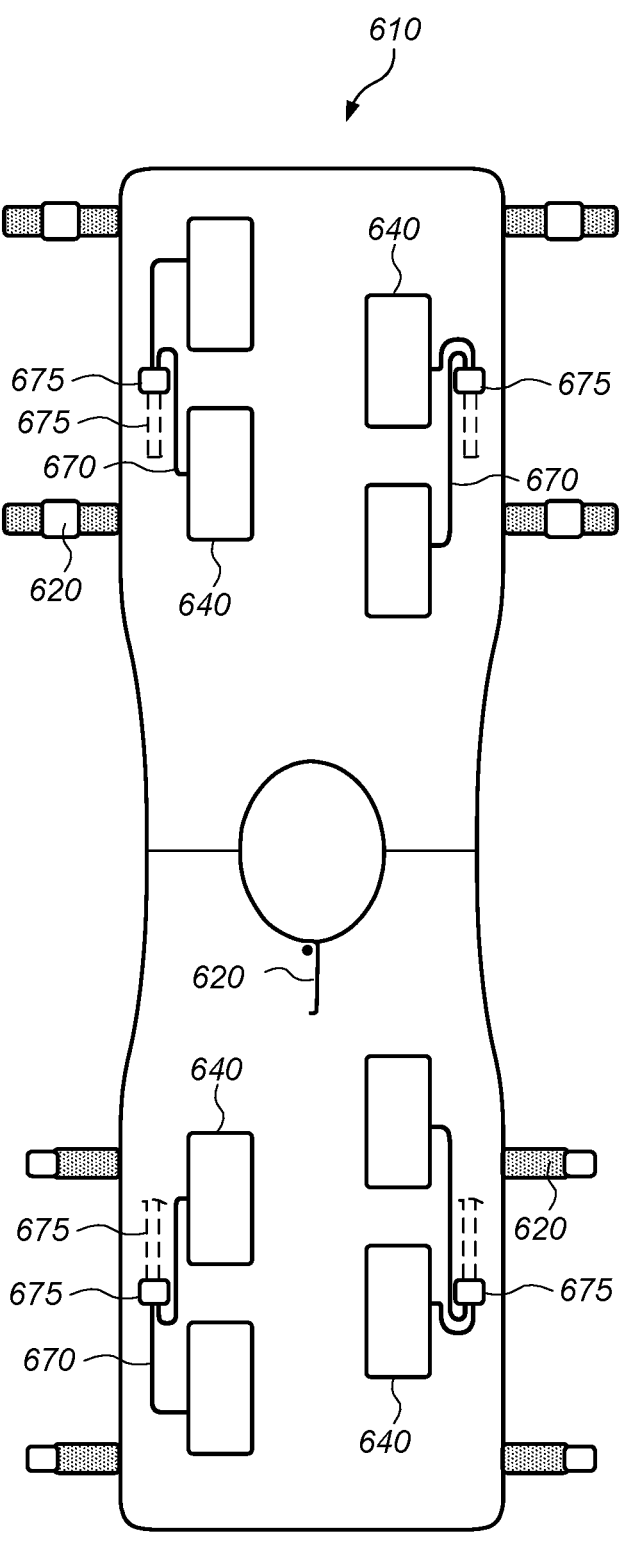
FIG. 17 depicts an interior view of a representation of an embodiment of a portable high frequency chest wall oscillator inner harness laid out in an open flat presentation.

In some embodiments, positioning system may include all (or substantially all) of the exterior surface of the inner harness (e.g., as depicted in FIGS. 10-15) being formed from half of a hook and loop system such that engines of the system 600 are virtually unlimited, in relation to the inner harness, as to where the portions may be positioned (the exterior surface may include a second layer formed from half of a hook and loop system). FIGS. 12-13 depict a front view and a rear view respectively of a representation of an embodiment of a portable high frequency chest wall oscillator inner harness positioned on a subject including a second layer 610a coupled or directly attached to the inner harness. In some embodiments, positioning system may include all (or substantially all) of the interior surface of the inner harness (e.g., as depicted in FIGS. 16-25) being formed from half of a hook and loop system such that engines of the system 600 are virtually unlimited, in relation to the inner harness, as to where the engines may be positioned (the interior surface may include a second layer formed from half of a hook and loop system). FIGS. 16-25 depict various views of a representation of an embodiment of a portable high frequency chest wall oscillator inner harness including a plurality of engines positioned on an interior surface of the inner wearable system.

Figures 20, 21:
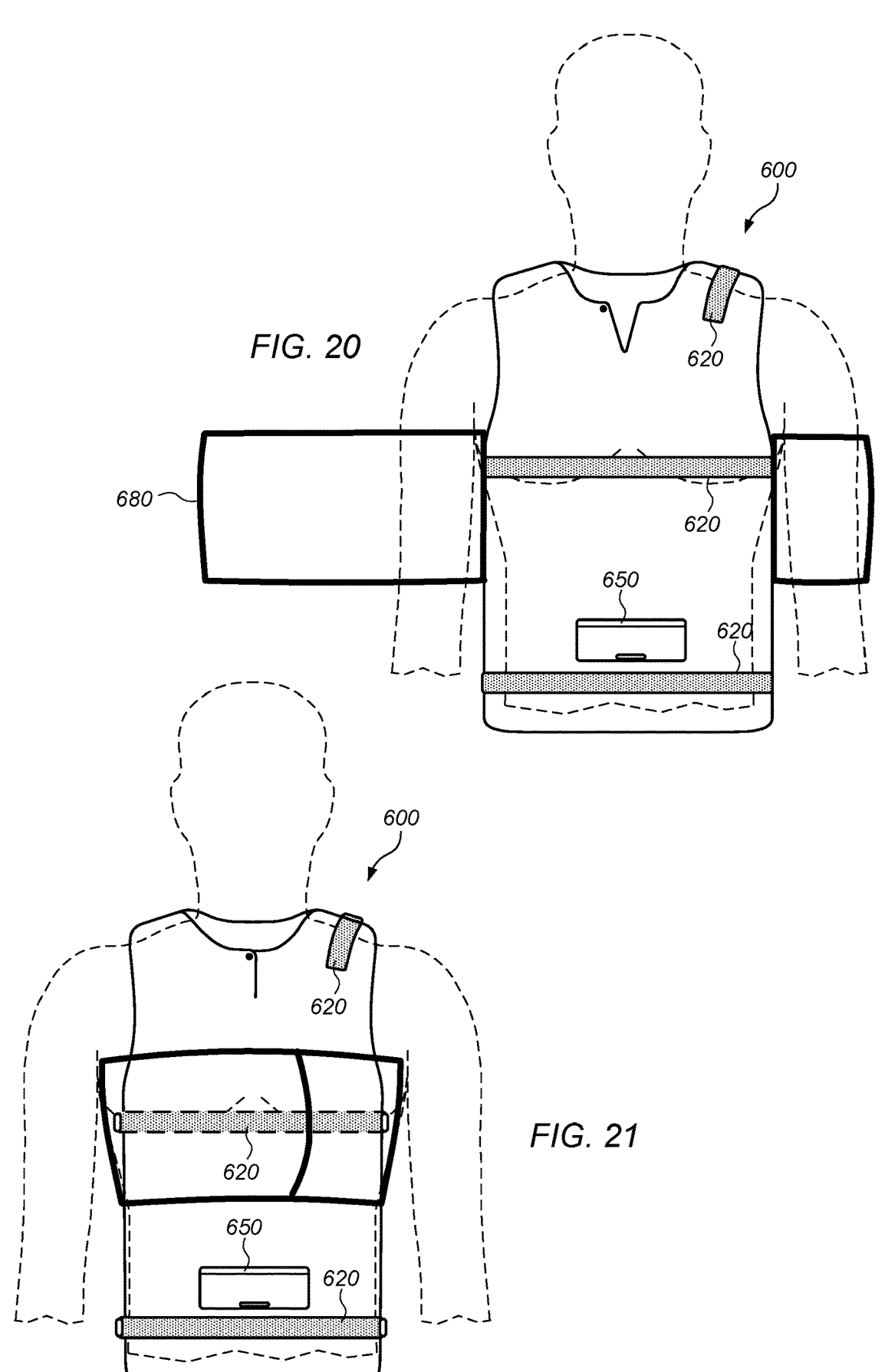
FIG. 20 depicts a front view of a representation of an embodiment of a portable high frequency chest wall oscillator inner harness including secured fasteners as well as an inactivated outer harness positioned on a subject.
FIG. 21 depicts a front view of a representation of an embodiment of a portable high frequency chest wall oscillator inner harness including secured fasteners as well as a single activated outer harness positioned on a subject.
Figures 22, 23:
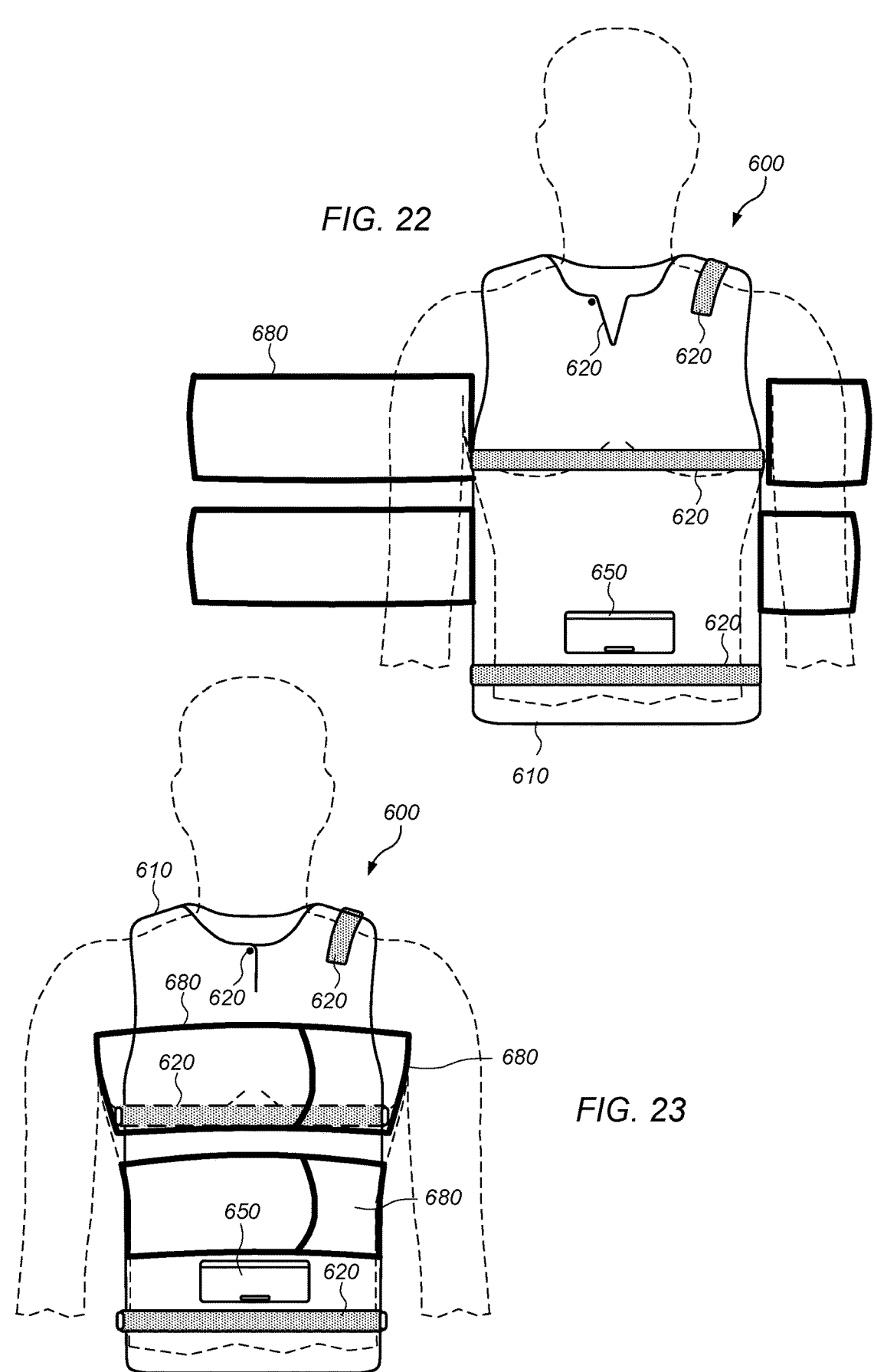
FIG. 22 depicts a front view of a representation of an embodiment of a portable high frequency chest wall oscillator inner harness including secured fasteners as well as two inactivated outer harnesses positioned on a subject.
FIG. 23 depicts a front view of a representation of an embodiment of a portable high frequency chest wall oscillator inner harness including secured fasteners as well as two activated outer harnesses positioned on a subject.
Figure 26:
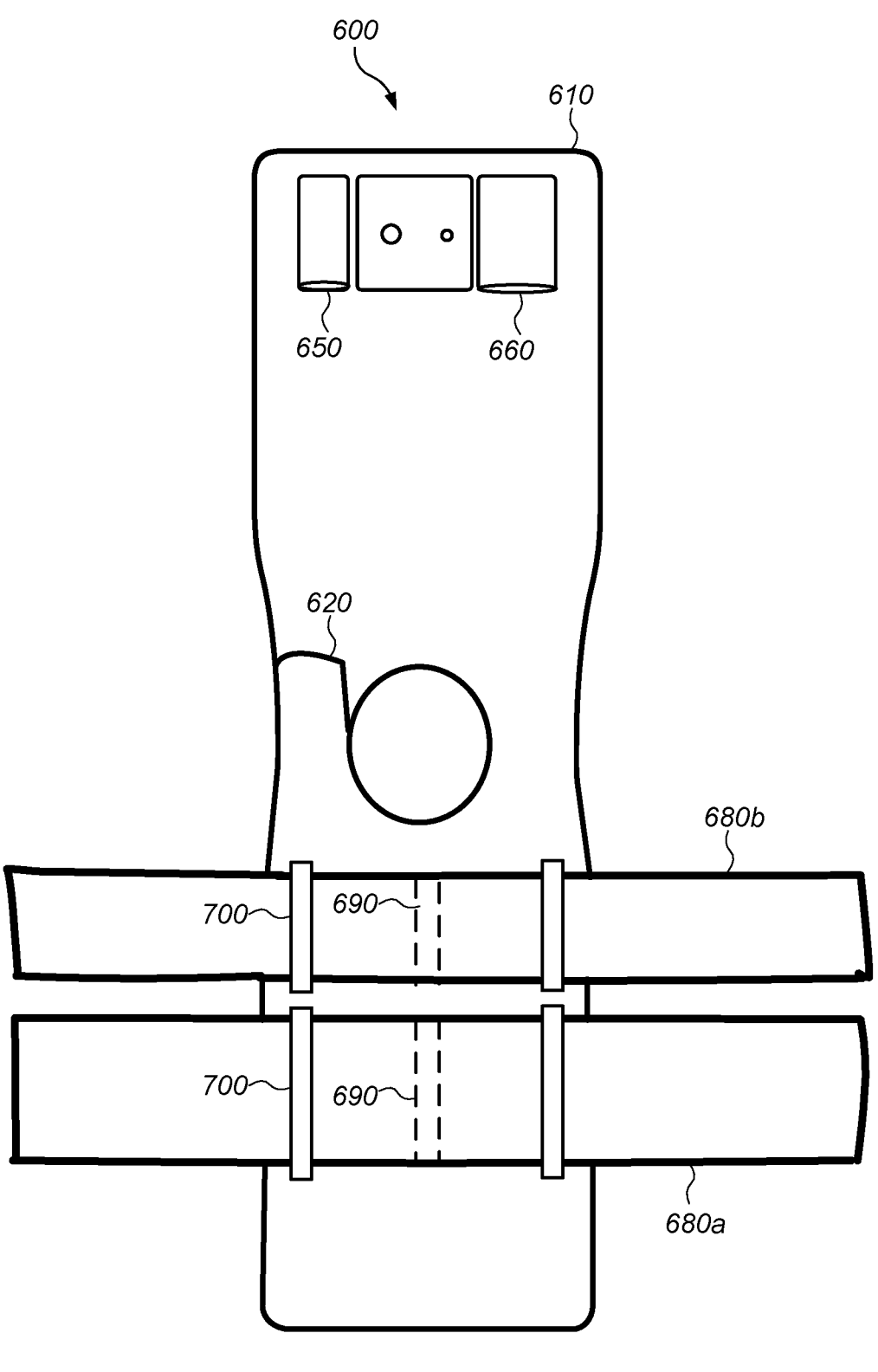
FIG. 26 depicts a front view of a representation of an embodiment of a portable high frequency chest wall oscillator inner harness including secured fasteners as well as two activated outer harnesses positioned on a subject.

In some embodiments, they system 600 may include an outer (or second) harness 680 (e.g., as depicted in FIGS. 14-15 and 20-25). The outer harness 680 may be positionable around at least a portion of an exterior of the inner harness 610. The outer harness may be formed from an elastic, a stretchable or flexible material which when worn compresses or applies pressure or a force or a compressive force to the inner harness and more importantly to any engines beneath the outer harness. Applying pressure to the engines may increase the efficiency of the engines as regards the treatment areas by pressing the engines against the subject. Generally, the outer harness may function, during use, to improve transmission of the oscillation force from the engines to the treatment area of the subject. The outer harness may function to further adjust the oscillation force based upon how tightly around the subject the outer harness is secured. The outer harness may function to provide a compressive force based upon how tightly around the subject the outer harness is secured. The outer harness functions to, in some embodiments, gather and/or tighten an inner harness around a subject to provide at least a better fit. In some embodiments, a system may include a single outer wearable harness (e.g., as depicted in FIGS. 20-21). In some embodiments, a system may include two or more outer wearable harnesses (e.g., as depicted in FIGS. 22-25). In some embodiments, a system may include two or more outer wearable harnesses wherein the outer wearable harnesses 680a-b are different widths (e.g., as depicted in FIG. 26).

The outer harness may allow for fewer sizes of the inner harness to be made available as the outer harness functions to tighten the engines against the subject such that the inner harness does not need to fit as snuggly. A first end of the outer harness may couple to a second end of the outer harness and/or to another portion of the outer harness during use (e.g., using hook and loop, buckles, clasps, etc.). At least a portion of the outer harness may be coupled or directly attached (e.g., permanently fixed (either directly (e.g., sewn to) or indirectly) or temporarily fixed (either directly (e.g., sewn to 690 as depicted in FIG. 25) or indirectly) to the inner harness. At least a portion of the outer harness may be coupled or directly attached to the inner harness in such a way as to allow movement in one or more directions of the outer harness relative to the inner harness (e.g., a double slit cut into the inner wearable harness through which the outer wearable harness is threaded through allowing latitudinal and/or longitudinal movement). In some embodiments, one or more portions of the outer wearable harness may be coupled or directly attached to the inner wearable harness using elongated members or loops 700 allowing the outer wearable harness to move relative to the inner harness while remaining coupled or directly attached to the inner wearable harness. The loops may allow a subject to more easily access the outer wearable harnesses during use (allowing the subject to more easily reach the outer wearable harnesses).

In some embodiments, the outer harness may include any way of providing a compressive force to against one or more of the engines increasing the efficiency of the oscillating force applied to the subject during use (e.g., an outer harness which laces up, tightening buckles, etc.). This is in contrast to some currently known vests which are rigid, wherein the rigidity of the vest controls the placement of the engines during use.

In some embodiments, one or more engines or portions of the system may be positioned (e.g., coupled or directly attached to) the outer harness (e.g., to an inner and/or outer surface of the outer harness).

In some embodiments, the wearable system 600 may include multiple engines 640 (e.g., two or more engines, for example, as depicted in FIG. 10). The system may include at least four engines 640, at least six engines 640, at least eight engines 640 or as many engines as necessary (e.g., as prescribed by a physician). In some embodiments, an engine 640 (e.g., as depicted in FIGS. 18A-B) may include electric motors, sonic wave generators, electro-mechanic or electro-dynamic vibrators, solenoid, etc. In some embodiments, engines 640 may be positioned in containers 645 (e.g., as depicted in FIG. 24). Containers 645 may be formed from primarily flexible or pliable materials. The container may include fixation means (e.g., hook and loop) which allow for positioning the engines 640 as necessary relative to system 600. The containers may substantially contain the engines 640 using a zipper and/or a closure flap with a button or hook and loop. In some embodiments, one or more containers may include padding (e.g., or be formed from a thicker pliable material). Padded containers may diffuse the oscillation force (e.g., vibration force) over a broader area of a subject, for example, to protect a subject from unintentional injury. The containers may be disposable, for example, for the purpose of controlling infection (e.g., after use discard the containers and reuse the engines. Containers may also be used for batteries and/or controllers. In some embodiments, engines, controllers, and/or batteries may be saved for reuse and/or recycling. In some embodiments, an engine 640 (e.g., as depicted in FIG. 18C) may include a substantially smooth outer covering such that the engine is easier disinfect the engine before and/or after use.

In some embodiments, the system 600 may include a control unit 650 (e.g., as depicted in FIGS. 11, 16, 19-23, and 25). The method may include activating at least the first engine using the control unit 650. The control unit may control activation/deactivation/adjustment of all of the engines of the system 100. In some embodiments, the control unit 650 may be couplable to the inner harness 610 (e.g., using a hook and loop strip 630 as depicted in FIG. 11 or positioned in a pocket as depicted in FIG. 25). The control unit 650 may be directly wired to the engines 640 and/or may be wirelessly coupled or directly attached to the engines. The control unit may use any number of known input methods (e.g., including touchpad). The control unit may be digital or analog. In some embodiments, the control unit may adjust one or more settings of the engines. The control unit may adjust the oscillation force output by the engine. The control unit may adjust an amplitude of the oscillation force output by the engine. The control unit may adjust a frequency of the oscillation force output by the engine. In some embodiments, engine parameters may be adjusted via software (e.g., a phone app) remotely (e.g., Wi-Fi, Bluetooth, etc.).

In some embodiments, the engines 110 may include a frequency range from 5 Hz to 20 Hz. In some embodiments, the intensity levels dictate the frequency which generally runs at 5 Hz for the lowest setting, 13 Hz for the medium setting and 20 Hz for the highest setting. In some embodiments, engines may be grouped together such that frequencies produced by the grouped engines result in a superposition of the produced frequencies in order to achieve frequencies and/or intensities not achievable under normal operating parameters of the engines. For example, a super-pulse may be achievable, lower frequencies may be achievable. The ability to produce such a variety of different frequencies is beneficial for treating different types of lung disorders. The principle of superposition may be applied to waves whenever two (or more) waves travel through the same medium at the same time. The waves pass through each other without being disturbed. The net displacement of the medium at any point in space or time, is simply the sum of the individual wave displacements. This is true of waves pulses or continuous sine waves. For example, two sinusoidal waves with the same amplitude and frequency can add either destructively or constructively depending on their relative phase. The phase difference between the two waves may increase with time so that the effects of both constructive and destructive interference may be seen. When the two individual waves are exactly in phase the result is large amplitude. When the two waves become exactly out of phase the sum wave is zero.

For example, bronchiectasis is a condition in which damage to the airways causes them to widen and become flabby and scarred preventing the airways from clearing mucus (mucus which is typically voluminous and relatively thin). In contrast cystic fibrosis is a genetic disorder that results in at least difficulty breathing and an inability to clear the lungs of mucus (mucus which is typically relatively thick). Different conditions result in different mucus and/or debris in a subject's lings which may benefit from different frequencies which may be prescribed by, for example, a physician.

In some embodiments, a method may include modifying the treatment parameters (e.g., amplitude, frequency, and time for each engine). Each engine may be programmed, using physical hardware control unit or software to run a custom cycle. This programming may be performed according to each subject. In addition, the system may provide a physician or caregiver with the ability to prescribe a defined treatment and/or to inhibit the user from modifying the treatment settings (e.g., lock-out feature w/password, pin code, etc.). Each of the motors may be individually programmable (e.g., length of run time, type of vibration (e.g., constant, pulsing, etc.), frequency, amplitude, etc.).

In some embodiments, the method and/or system may adaptively modify the treatment protocol based on subject and/or physician feedback. For example, a subject enters mucus secretion levels after each treatment and the system adaptively optimizes the treatment settings over time.

In some embodiments, the method and/or system may monitor compliance information. For example, the system could monitor (in real-time) the treatment for each subject, including parameters run, time of treatment, time of day and any subject feedback. This could be accomplished through hardware or software (e.g., a web-based subject/physician portal which links w/Bluetooth to each vest). The information may be provided to the subject, physician, insurance company or other third-party.

In some embodiments, the system 600 may include at least one battery 660. The method may include powering the engines 640 using one or more batteries 660 coupled or directly attached to the inner harness of the wearable system. In some embodiments, a battery 660 may include a rechargeable battery and/or a disposable battery. The battery 660 may include two or more batteries. The batteries 660 may be easily swapped out whether rechargeable or disposable. The battery 660 may be coupled or directly attached to the system 600 (e.g., using a hook and loop strip 630 as depicted in FIG. 11). The system may include an adapter such that, when necessary, the system may be coupled or directly attached to an electrical outlet (e.g., through an electrical adapter if necessary). The system 100 may be powered using AC or DC power sources such that the system may be powered using virtually any known power source currently available.

In some embodiments, the system 600 may include a system of electrical couplings 670. Electrical couplings 670 may couple control unit 650 and/or battery 660 to engines 640 (e.g., as depicted in FIGS. 10-13). The electrical couplings may run on an exterior surface of the inner harness (e.g., as depicted in FIGS. 10-11). The electrical couplings may run under a second layer 610a of inner harness 610 (e.g., as depicted in FIGS. 12-13) with coupling ends extending out of openings in the second layer 610a. In some embodiments, at least some portions of the electrical couplings may be bound or bundled together (e.g., such that the electrical couplings are easier to separate from the rest of the system 600 for disposal or recycling. In some embodiments, the electrical couplings (e.g., wires) may be sewn in to the disposable inner wearable system. The inner wearable system may include conduits 675 (e.g., fabric, impervious materials (e.g., plastics) as depicted in FIG. 24) for wires coupled or directly attached to and/or sewn into the inner wearable system (e.g., to electrically connect a battery and/or a controller to at least one of the plurality of engines). In some embodiments, conduits 675 may be positionable relative to the inner wearable system. The conduits may be connected to the inner wearable system using hook and loop systems. The wires may provide multiple connection points for the plurality of engines so that the plurality of engines is repositionable while still using the wires in the fabric conduits.

In some embodiments, the system may be self-contained. The system may be self-contained such that a subject may wear the system 600 and move freely and in a substantially unrestricted manner. The system may be self-contained such that a subject may wear the system 600 while functioning and not physically connected to any external devices (e.g., air pumps).

In some embodiments, all, substantially all, or at least one portion of the system 600 may be disposable or recyclable. Making portions of the system 600 disposable may be disposable due to, for example, that much of the equipment used in healthcare environments which comes into direct contact with subjects is disposable (or covered by disposable sheaths). It is typically much easier and/or less expensive to throw away equipment which comes into contact with subjects as opposed to cleaning the equipment. In some embodiments, the inner wearable harness is disposable. In some embodiments, the outer wearable harness is disposable. In some embodiments, at least some of the plurality of engines are disposable. In some embodiments, the inner and/or outer harness and the engines may be disposable.

In some embodiments, one or more portions of the system 600 are recyclable. For example, self-contained portions of the system (e.g., engines 640) may be recyclable in order to reduce waste.

In some embodiments, one or more portions of the systems describe herein may include antimicrobial coatings (e.g., in fabrics of the vests). In some embodiments, one or more portions of the systems described herein may be able to withstand one or more common medical sterilization techniques (e.g., high temperature, high pressure, chemical, etc.). In some embodiments, one or more portions (e.g., in fabrics of the vests or the containers for one or more engines) may include an impervious materials, coatings, or linings such that one or more portions of the system are protected from or at least inhibited from exposure to one or more contaminants. For example, a lining or material may be substantially impervious to water or blood borne pathogens or contaminants. For example, a lining or material may be substantially impervious to gasses and/or air borne pathogens or contaminants. In some embodiments, a container such as a positionable engine container 645 may include an impervious or impermeable lining which inhibits contamination of an engine positioned in the container such that the engine may be more easily recycled.

Compliance Monitoring and Data Collection

Figure 27:
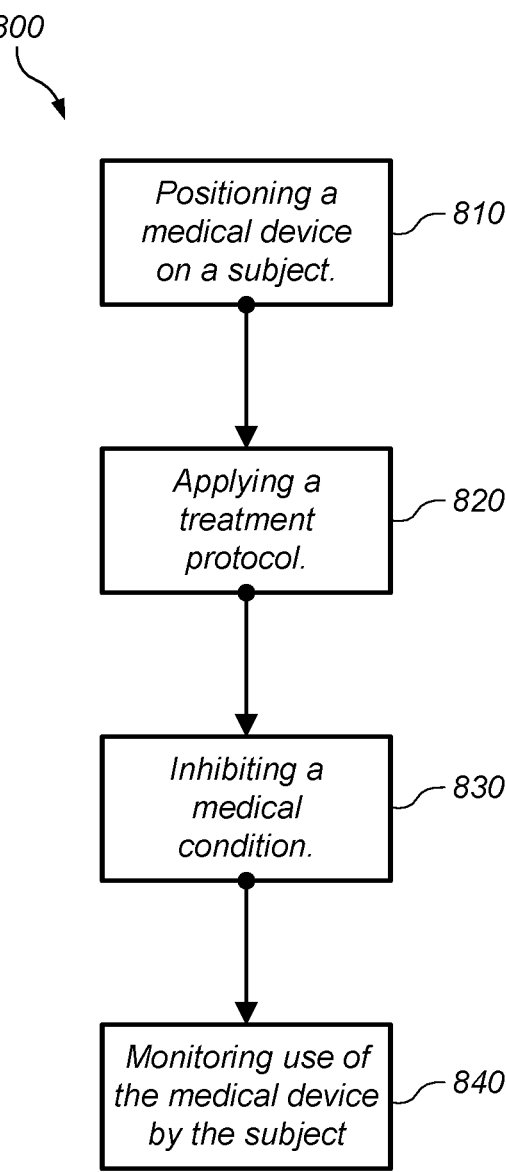
FIG. 27 depicts a flow chart of an embodiment of a method of monitoring a subject's compliance for following a caregiver's prescribed regimen for a medical device.

In some embodiments, a method may include monitoring use of a medical device. A medical device may include a portable high frequency chest wall oscillator system as described herein. FIG. 27 depicts a flow chart of an embodiment of a method 800 of monitoring a subject's compliance for following a caregiver's prescribed regimen for a medical device. Briefly as described herein, the method may include positioning 810 a wearable harness of a medical device on a subject. The method may include assessing treatment areas of the subject's chest for selective placement of at least some of the plurality of the engines, such that the at least some of the plurality of engines are adjacent to treatment areas that need secretion mobilization. The method may include selectively positioning at least some of a plurality of engines on and/or adjacent to at least one treatment area. At least one of the plurality of engines may be releasably couplable to the wearable harness such that the at least one of the plurality of engines is positionable relative to the subject using a positioning system. The method may include applying 820 an oscillation force to at least one of the treatment areas using at least some of the plurality of engines. In some embodiments, the method may include mobilizing 830 at least some secretions in an airway within the subject substantially adjacent to the treatment areas.

In some embodiments, the method may include monitoring 840 use of the medical device by the subject using a controller associated with the medical device. Known HFCWO systems do not allow for a user adjusting where forces are applied to on the subject. This is problematic because although some known HFCWO systems may come in different sizes to accommodate differently sized subjects, there are far too many people of different sizes and so it is impractical to produce enough differently sized systems for all of the differently sized subjects. A system which allows for adjustment and/or positioning of one or more engines and/or one or more groups of engines may allow for prescriptive oscillation or prescriptive positioning of engines by a caregiver. For example, a caregiver may employ means to visualize (e.g., x-rays) secretions accumulating in the lungs of a subject and then position engines appropriately around any areas where secretions are accumulating. In some embodiments, engines may not only be simply placed adjacent to treatment areas but also may be positioned adjacent to areas adjacent to the treatment area to assist in flushing out secretions from the subject (e.g., pushing the secretions outside of the subject). In some embodiments, engines may be positioned in a serpentine pattern on a subject using systems described herein to create what may be described as a wave effect of oscillation forces.

Figure 30:
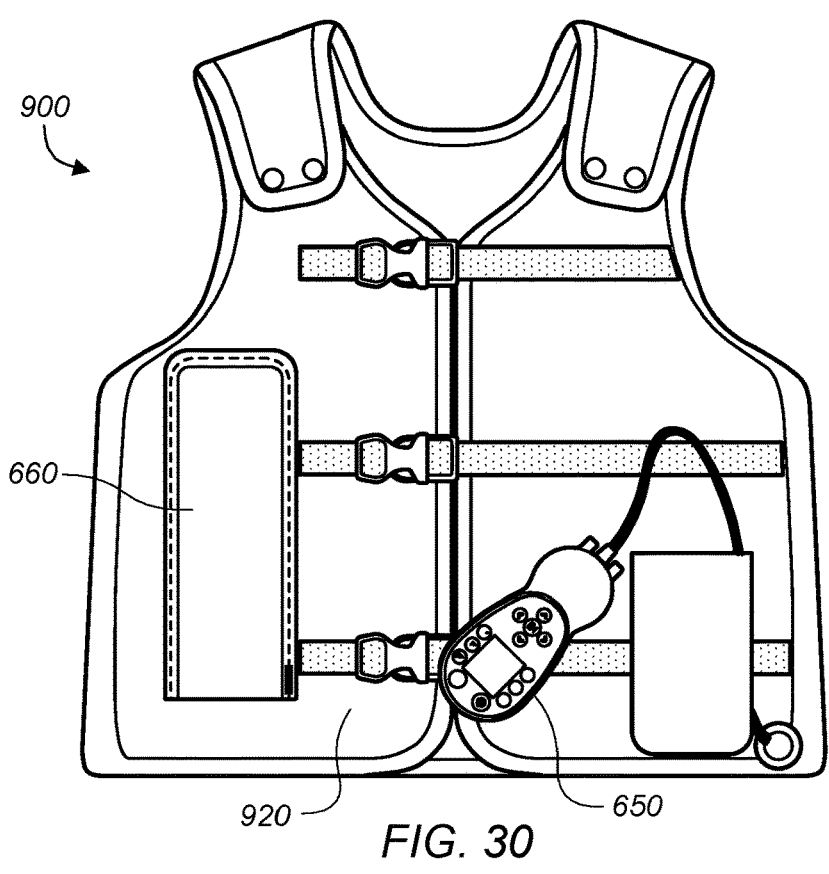
FIG. 30 depicts a front view of a representation of an embodiment of a portable high frequency chest wall oscillator wearable harness including a compression mechanism, a controller, and a battery.
Figure 31:
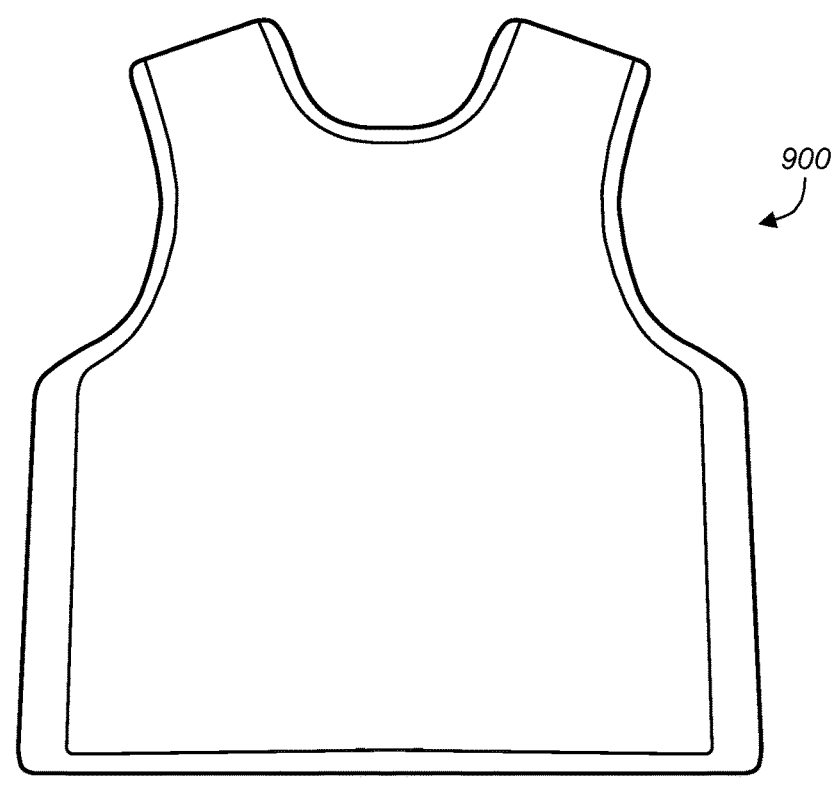
FIG. 31 depicts a rear view of a representation of an embodiment of a portable high frequency chest wall oscillator wearable harness.
Figure 32:
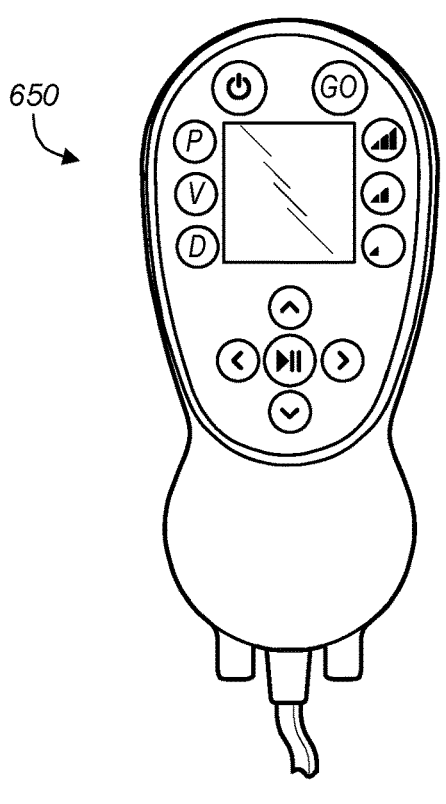
FIG. 32 depicts a representation of an embodiment of a controller for a portable high frequency chest wall oscillator.
Figure 33:
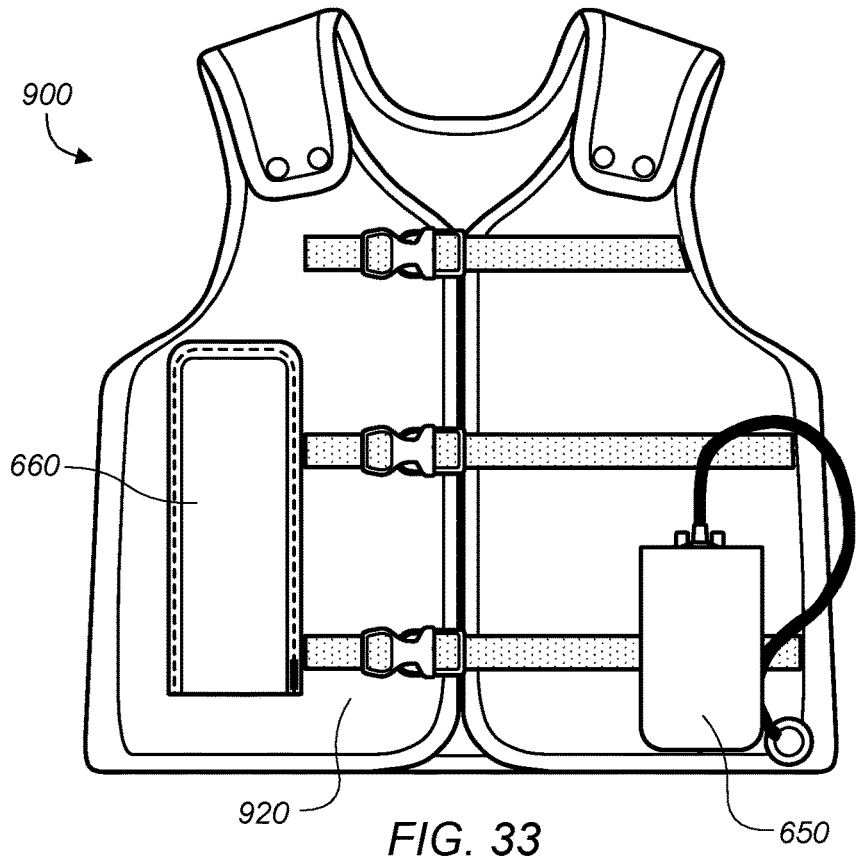
FIG. 33 depicts a front view of a representation of an embodiment of a portable high frequency chest wall oscillator wearable harness including a compression mechanism, a controller (positioned in a container), and a battery.

In some embodiments, a caregiver may prescribe not only the position of the engines but also the frequency of one or more of the engines. The pulse or the beat frequency of one or more of the engines may be adjusted based upon a prescribed frequency. In some embodiments, a caregiver may prescribe or program one or more or all of the engines to turn on or off. The prescribed regimen may be input in a controller on the system. The controller may be able to communicate electronically (e.g., with a wired and/or wireless communication connection) with a server, network, computer such that a prescribed regimen may be input, updated, and/or retrieved. FIG. 30 depicts a front view of a representation of an embodiment of a portable high frequency chest wall oscillator wearable harness 900 including a compression mechanism 920 (described herein), a controller 650, and a battery 660. FIG. 31 depicts a rear view of a representation of an embodiment of a portable high frequency chest wall oscillator wearable harness 900. FIG. 32 depicts a representation of an embodiment of a controller 650 for a portable high frequency chest wall oscillator. As is depicted in FIG. 32 the controller may include switches for power, start, pulse, vibration, pause, zone, program, navigation, duration, and intensity. The controller depicted is coupled directly to the harness while communicating wirelessly with a server, network, computer, etc. The controller may be positionable in a pocket (e.g., a sealable pocket) for general storage as depicted in FIG. 33. The battery 660 may be positionable in a pocket (e.g., a sealable pocket) as depicted in FIGS. 30, 33, and 35. The wearable harness system may include a battery charging system 665 as depicted in FIGS. 34-35. The battery charging system 665 may be couplable to the battery while the battery is positioned in a pocket through an opening in the pocket using an electrical cable.

In some embodiments, a caregiver and/or subject may track a prescribed regimen to ensure that a subject is complying with a prescribed regimen. The prescribed regimen may include a total time of activation, an oscillation frequency, an oscillation amplitude, placement of engines, number of engines, frequency of activation, total number of activations during a given time period, duration of activation per activation, etc.

In some embodiments, a controller may be used to collect data associated with use of a medical device. Data associated with a use of a medical device may include how the medical device is used as described herein as well as medical data associated with the medical device (e.g., personal medical information of the subject before and/or after use of the medical device). The medical data may be automatically gathered by the medical device and/or an associated medical device and therefore not require interaction by the subject and/or caregiver. In some embodiments, at least some of the medical data may be entered in by the subject or a caregiver.

Medical data gathered as described may be used to adjust a prescribed regimen. Medical data may be used in combination with observations from the subject and/or caregiver to determine if and how a prescribed regimen should be adjusted (e.g., after a session with the medical device does the patient feel better and if so, how much).

In some embodiments, monitoring use of the medical device may include confirming that the subject has worn the medical device and applied the oscillation force while wearing the medical device.

Problems associated with many compliance monitoring systems is that they can only tell if a medical device has been activated and cannot determine if the medical devise has actually been used by the subject. For example, a HFCWO system may be turned on by a user without actually being worn by the user (a child may do this in an attempt to avoid wearing the medical device).

In some embodiments, monitoring use of the medical device may include determining a change (e.g., a drop or increase) in a power consumption of the at least some of the plurality of engines. Many of the systems described herein use compression to activate or increase the efficiency of the engines during activation. When an engine is compressed against a subject the engine must necessarily work harder increasing the load or voltage draw resulting in an at least temporary increase in voltage. This increase in voltage may be monitored by a controller or other such unit. A monitored increase or change in voltage may be noted as an activation of the medical device. Such a monitored change in voltage or current may differentiate between a medical device simply being turned on and a medical device being worn and activated properly.

In some embodiments, a compliance monitoring system may determine if a medical device is not only being worn but also being used properly. Monitoring systems may function to determine if a user is employing the medical device properly or not. Monitoring systems may determine if a medical device is being used effectively such that the user gets the most effective treatment. Monitoring systems may not only determine if a medical device is simply on or not but may also determine that the medical device is being used effectively for example including, but not limited to, determining if a correct compression is being applied to one or more of the engines. In the past there have been monitoring devices that have simply monitored whether or not a medical device has been activated. Subjects have simply circumvented this simple monitoring device (e.g., in an attempt to avoid a lecture from their caregiver and/or assure continued coverage by an insurance agent, etc.) by turning the device on for a period of time without actually wearing and/or correctly using the medical device. Monitoring may include ensuring that subjects are using a medical device as directed (e.g., as prescribed by a caregiver). Correct compression may be determined by monitoring a change in power consumption or voltage. Ranges in power consumption or voltage may be determined which allow for monitoring not only if the medical device is on but also if the medical device is being used correctly and in an effective manner with a correct compression applied to one or more of the plurality of engines (e.g., based upon a caregiver's prescription). Such monitoring may be viewed in some embodiments as an authentication or verification step.

In some embodiments, different types of sensors may be used to monitor compliance to ensure proper and/or prescribed usage of a medical device. In some embodiments, sensors may include acceleration or vibration sensors, force/pressure sensors, or tachometer sensors. Sensors may include proximity, pressure, acceleration, temperature, strain, pressure, force, or tachometer sensors. Monitoring use of the medical device may include monitoring a change in vibration of the at least some of the plurality of engines (e.g., using a vibration sensor). Monitoring use of the medical device may include monitoring a change in acceleration of the at least some of the plurality of engines (e.g., using an acceleration sensor). Monitoring use of the medical device may include monitoring a change in an applied force of the at least some of the plurality of engines (e.g., using a force sensor). Force sensors may include a load cell or a strain gauge. In some embodiments, sensors used may be based on capacitive sensing. Capacitive sensing (sometimes capacitance sensing) is a technology, based on capacitive coupling, that can detect and measure anything that is conductive or has a dielectric different from air. Many types of sensors use capacitive sensing, including sensors to detect and measure proximity, position or displacement, humidity, fluid level, and acceleration. Digital audio players, mobile phones, and tablet computers use capacitive sensing touchscreens as input devices. Capacitive sensors can also replace mechanical buttons.

In some embodiments, acceleration and/or vibration sensors may be used to determine relative movement or motion of engines and/or portions of the medical device. Such sensors may be sensitive enough to determine not only the difference between when an engine is on or off but also determine whether or not compression has been applied to the engines when they are activated/on.

In some embodiments, pressure and/or force sensors may be used to determine relative pressure or force exerted by engines and/or portions of the medical device, as described herein. Such sensors may be sensitive enough to determine not only the difference between when an engine is on or off but also determine whether or not compression has been applied to the engines when they are activated/on.

In some embodiments, temperature sensors may be used to determine relative temperature of engines and/or portions of the medical device. Such sensors may be sensitive enough to determine not only the difference between when an engine is on or off but also determine whether or not compression has been applied to the engines when they are activated/on (as an engine is compressed the engine is forced to work harder increasing the heat output and temperature of the engine). Temperature sensors may be used to determine if a user has put on the medical device such that the temperature sensor is adjacent to a user when worn properly such that the temperatures sensor senses a change in temperature associated with being in close proximity to a user's body (e.g., the elevated temperature of a user relative to the ambient temperature).

In some embodiments, proximity sensors may be used to determine a position of engines relative to portions of the medical device. Knowing a position of an engine relative to the medical device may allow for monitoring a prescribed regimen which typically will include prescribed positioning of the engines relative to the medical device.

In some embodiments, a caregiver may prescribe a treatment protocol which may be entered by the caregiver manually into a control unit and/or remotely (e.g., via a wireless connection directly (e.g., via Bluetooth, Wi-Fi) or from anywhere via the internet) or the user may input. Sensors (e.g., proximity) may provide feedback (e.g., auditory, tactile, visual, etc.) to the user or the caregiver as engines are positioned to ensure the engines are positioned per the prescribed treatment protocol. For example, a web of sensors may alert a user/caregiver when the engines have been placed properly or improperly.

In some embodiments, a medical device may direct a user/caregiver where to place positionable engines on a medical device based on a treatment protocol. For example, a wearable harness or garment may include a plurality (e.g., a grid of lights or even a drawn grid) of markers which are used to direct a user/caregiver where to position positionable engines. A caregiver may prescribe a treatment protocol and alert the user via a control unit for the medical device or via more conventional means which instructs the user where to position the engines on the wearable harness or garment to achieve the desired effect by telling the user to place the engines using, for example, a labeled grid on the wearable harness or grid.

In some embodiments, a method may include modifying the treatment parameters (e.g., amplitude, frequency, and time for each engine). Each engine may be programmed, using physical hardware control unit or software to run a custom cycle. This programming may be performed according to each subject. In addition, the system may provide a physician or caregiver with the ability to prescribe a defined treatment and/or to inhibit the user from modifying the treatment settings (e.g., lock-out feature w/password, pin code, etc.). Each of the motors may be individually programmable (e.g., length of run time, type of vibration (e.g., constant, pulsing, etc.), frequency, amplitude, etc.).

In some embodiments, the method and/or system may adaptively modify the treatment protocol based on subject and/or physician feedback. For example, a subject enters mucus secretion levels after each treatment and the system adaptively optimizes the treatment settings over time.

In some embodiments, the method and/or system may monitor compliance information. For example, the system could monitor (in real-time) the treatment for each subject, including parameters run, time of treatment, time of day and any subject feedback. This could be accomplished through hardware or software (e.g., a web-based subject/physician portal which links w/Bluetooth to each vest). The information may be provided to the subject, physician, insurance company or other third-party.

In some embodiments, a medical device controller may be able to report effective compliance conditions when possible, to a centralized location. Thus, the status information received may come directly from the medical device controller. The medical device controller may include a component configured to transmit information, thereby enabling the medical device controller to send status information to a centralized location (e.g., computer, control center, processor, etc.). In some approaches, a network (e.g., cloud-based network) may be used to transmit the information to the central location.

In some embodiments, the method and/or system may monitor use of the medical device by the subject including determining if the medical device has been used as prescribed (e.g., by a caregiver). Monitoring use of the medical device by the subject may include determining if the medical device is being used as prescribed (e.g., by a caregiver). The method may include notifying the subject if the medical device is being used as prescribed by the caregiver as the medical device is being used in real time. The method may include notifying the caregiver if the medical device is being used as prescribed by the caregiver as the medical device is being used in real time. The subject/caregiver may be notified in one or more of a number of ways including one or more lights, sounds, and/or electronic notifications (e.g., via a mobile phone application, etc.). One or more factors may be prescribed as regards the medical device including, but not limited to, an oscillation force, a force requirement, an amplitude, a frequency, or an oscillation waveform. Any data gathered may be stored and disseminated at a later time in form of regular usage and/or health reports to a subject, caregiver, insurance provider, government official, etc.

In some embodiments, the personal medical information of a user may be input into a control unit and based upon the specifics of a user's medical condition the control unit may determine or assist a caregiver in where to position one or more engines on the wearable garment.

In some embodiments, sensors may include piezoelectric sensors. Based on piezoelectric technology various physical quantities may be measured, the most common are pressure and acceleration. For pressure sensors, a thin membrane and a massive base may be used, ensuring that an applied pressure specifically loads the elements in one direction. For accelerometers, a seismic mass is attached to the crystal elements. When the accelerometer experiences a motion, the invariant seismic mass loads the elements according to Newton's second law of motion F=ma.

In some embodiments, sensors may be used alone or in combination with other monitoring means. In some examples at certain low output levels of the engines may result in a difficulty in detecting voltage changes such that combining voltage monitoring sensors with one or more other sensors would bolster the ability to confirm proper compliance of usage of the medical device.

In some embodiments, monitoring use of the medical device may include monitoring a change in vibration of the at least some of the plurality of engines. A change in vibration may be monitored using a vibration, force, pressure or tachometer sensor.

In some embodiments, wherein monitoring use of the medical device may include monitoring a change in acceleration of the at least some of the plurality of engines. A change in acceleration may be monitored using an acceleration sensor.

In some embodiments, the method may include notifying a care provider as to whether or not the subject is complying with a prescription associated with the medical device. Notification may be accomplished by using a wireless connection to a controller associated with the medical device. The prescription may be entered directly into the controller or entered through a wireless connection.

In some embodiments, the method may include positioning an inner and an outer wearable harness on a torso of a subject. The method may further include applying an oscillation force to at least one of the treatment areas using at least some of the plurality of engines. The method may include providing a compressive force to at least some of the activated plurality of engines to the treatment area by activating the outer wearable harness.

Computer systems implemented for implementing various aspects of the processes described herein may, in various embodiments, include components such as a CPU with an associated memory medium such as Compact Disc Read-Only Memory (CD-ROM). The memory medium may store program instructions for computer programs. The program instructions may be executable by the CPU. Computer systems may further include a display device such as monitor, an alphanumeric input device such as keyboard, and a directional input device such as mouse. Computer systems may be operable to execute the computer programs to implement computer-implemented systems and methods. A computer system may allow access to users by way of any browser or operating system.

Computer systems may include a memory medium on which computer programs according to various embodiments may be stored. The term "memory medium" is intended to include an installation medium, e.g., Compact Disc Read Only Memories (CD-ROMs), a computer system memory such as Dynamic Random Access Memory (DRAM), Static Random Access Memory (SRAM), Extended Data Out Random Access Memory (EDO RAM), Double Data Rate Random Access Memory (DDR RAM), Rambus Random Access Memory (RAM), etc., or a non-volatile memory such as a magnetic media, e.g., a hard drive or optical storage. The memory medium may also include other types of memory or combinations thereof. In addition, the memory medium may be located in a first computer, which executes the programs or may be located in a second different computer, which connects to the first computer over a network. In the latter instance, the second computer may provide the program instructions to the first computer for execution. A computer system may take various forms such as a personal computer system, mainframe computer system, workstation, network appliance, Internet appliance, personal digital assistant ("PDA"), television system or other device. In general, the term "computer system" may refer to any device having a processor that executes instructions from a memory medium.

The memory medium may store a software program or programs operable to implement embodiments as described herein. The software program(s) may be implemented in various ways, including, but not limited to, procedure-based techniques, component-based techniques, and/or object-oriented techniques, among others. For example, the software programs may be implemented using ActiveX controls, C++ objects, JavaBeans, Microsoft Foundation Classes (MFC), browser-based applications (e.g., Java applets), traditional programs, or other technologies or methodologies, as desired. A CPU executing code and data from the memory medium may include a means for creating and executing the software program or programs according to the embodiments described herein.

Portable High Frequency Physiological Oscillator with Side Compression and/or Activation In some embodiments, a system may include a wearable harness worn, during use, on a subject (e.g., on and/or adjacent to the torso). The wearable harness may include a compression mechanism. The system may include a plurality of engines which when activated apply an oscillation force to at least one treatment area of the subject. At least one of the plurality of engines may be releasably couplable to the wearable harness such that the at least one of the plurality of engines is selectively positionable relative to the subject using a positioning system. One or more of the engines may be coupled to an interior surface or an exterior surface of the wearable harness. One or more of the engines may be coupled to an interior space within the wearable harness.

The positioning system may allow for positioning the at least one of the plurality of engines such that the oscillation force is applied to at least one of the treatment areas of the subject. The oscillation force may mobilize, during use, at least some secretions in an airway within the subject at least adjacent to the treatment area. In some embodiments, the compression mechanism adjusts the oscillation force applied by at least some of the activated plurality of engines to the treatment area.

Figure 28:
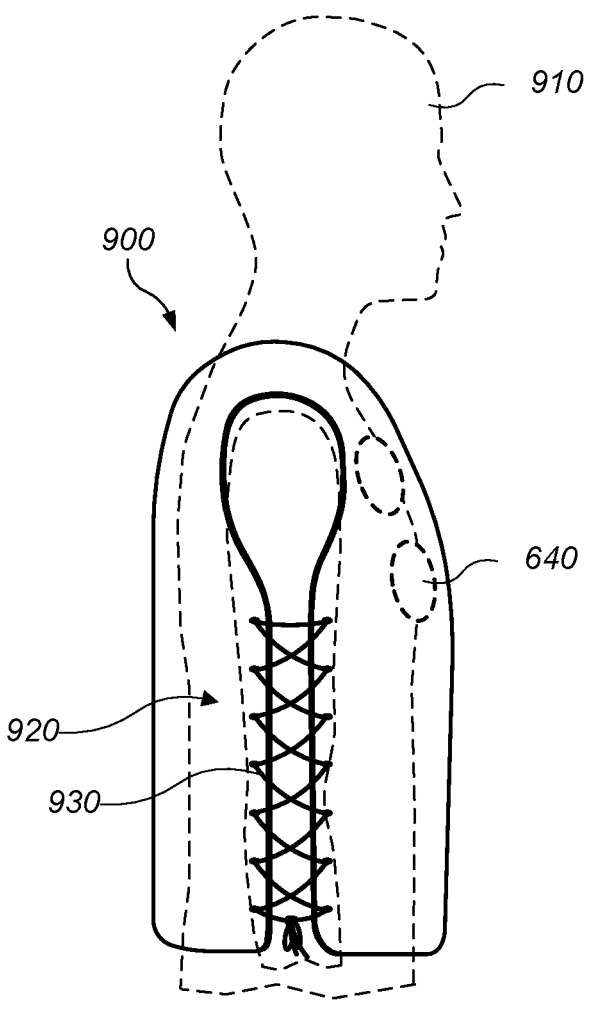
FIG. 28 depicts a view of a representation of an embodiment of a portable high frequency chest wall oscillator wearable harness including a compression mechanism including a lacing mechanism along the side.
Figure 29:
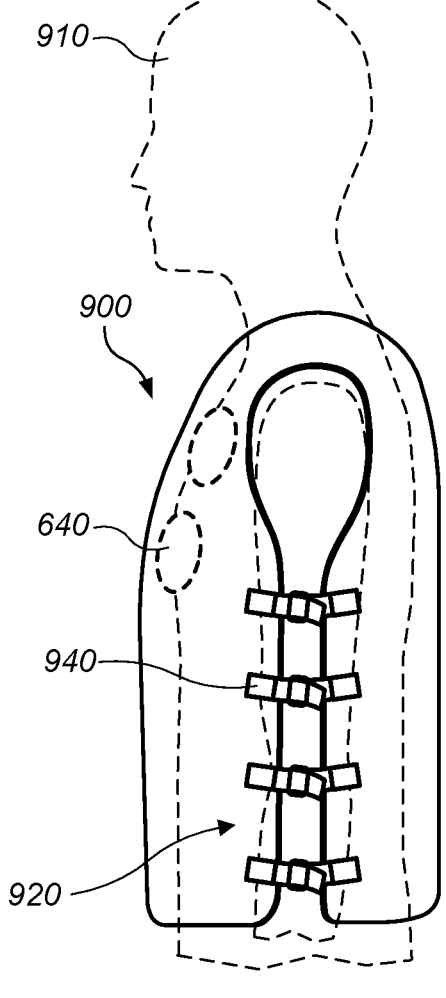
FIG. 29 depicts a view of a representation of an embodiment of a portable high frequency chest wall oscillator wearable harness including a compression mechanism including a buckling mechanism along the side.

In some embodiments, the compression mechanism tightens at least a portion of the wearable harness against the torso of the subject such that the oscillation force applied by the at least some of the activated plurality of engines 640 to the treatment area is adjusted. In some embodiments, the compression mechanism may include at least one set of lacing along a longitudinal length of the wearable harness. FIG. 28 depicts a view of a representation of an embodiment of a portable high frequency chest wall oscillator wearable harness 900 positioned on a subject 910 including a compression mechanism 920 including a lacing mechanism 930 along the side. In some embodiments, the compression mechanism may include at least one set of buckles along a longitudinal length of the wearable harness. FIG. 29 depicts a view of a representation of an embodiment of a portable high frequency chest wall oscillator wearable harness 900 positioned on a subject 910 including a compression mechanism 920 including a buckling mechanism 940 along the side. The buckling mechanism may include buckles, snaps, hook and loop systems, snaps ratcheting buckles, hook and opening, zipper(s), etc.

In some embodiments, the compression mechanism may include at least one set of ratcheting buckles along a longitudinal length of the wearable harness. The compression mechanism may be installed along a front or a back of the wearable harness. The compression mechanism may be installed along a side of the wearable harness. In some embodiments, the compression mechanism may be positioned along a longitudinal length of the wearable harness along a left or right side of a user during use. Installing a compression mechanism along one or more sides of the wearable harness may allow for access to the compression mechanism during different situations. For example, a compression mechanism may be positioned along a side of the wearable harness in order to allow a caregiver to access/activate the compression mechanism when the subject is lying prone, for example, in a bed in a hospital. In some embodiments, the wearable harness may include multiple compression mechanisms along multiple sides of the wearable harness allowing at least one of the compression mechanisms to be accessed during different situations (e.g., depending on how the subject is positioned and/or what area of the wearable harness is accessible by, for example, a caregiver). In some embodiments, the wearable harness may include an inner and an outer harness.

In some embodiments, a compression mechanism may be located anywhere on a wearable harness while an activation mechanism for that compression mechanism may be located remotely to the compression mechanism (e.g., on a side) of a wearable harness such that it is more accessible to a caregiver when the subject is in, for example, a prone position. In some embodiments, an activation mechanism of the compression mechanism may be positioned along a longitudinal length of the wearable harness along a left or right side of a user during use.

Force Sensing Elements for Monitoring

In various embodiments, one or more force sensors are implemented in the straps (e.g., straps 120, 160, or 620 described herein) of a portable high frequency chest wall oscillator wearable harness. Detection of force (such as tension or strain) in the straps may be useful in monitoring use of the wearable harness. Parameters determined by the detection of force in the straps may also be implemented in optimizing comfort in wearing the harness and/or performance of the wearable harness (e.g., compliance monitoring). Integrating force sensors with the straps of the wearable harness may provide a non-intrusive and indirect measurement of force being applied by the motors in the wearable harness.

FIG. 36 depicts a representation of an embodiment of a portable high frequency chest wall oscillator wearable harness 900 with force sensing element 3600 integrated with strap 120 on the wearable harness. Strap 120 may include strap portions 120A and 120B that are coupled together with connector 3601 to close wearable harness 900 around a chest of a subject. For example, connector 3601 may be a side-release buckle or another type of connectors for coupling the strap portions together. In various embodiments, force sensing element 3600 is integrated with strap 120.

FIG. 37 depicts a representation of an embodiment of force sensing element 3600. In the illustrated embodiment, force sensing element 3600 includes sensor cover 3602, harness attachment portion 3604, and strap attachment portion 3606. Harness attachment portion 3604 may be attached to or coupled to wearable harness 900. For example, harness attachment portion 3604 may be attached to an outside surface of wearable harness 900 (as shown in FIG. 36) using buttons, snaps, stitching, or combinations thereof to secure force sensing element 3600 to the wearable harness. Strap attachment portion 3606 may have opening 3608 that allows strap portion 120A to be looped through and secured to the force sensing element (as shown in FIG. 36). In some embodiments, snaps or other fasteners may be used to secure the loop to the opening in force sensing element 3600.

FIG. 38 depicts a representation of an embodiment of force sensing element 3600 with a portion of sensor cover 3602 removed. In the illustrated embodiment, force sensing element 3600 includes sensor 3800, sensor body element 3802, and sensor body element 3804. In certain embodiments, sensor 3800 is a flexible force sensor. A non-limiting example of a force sensor is a FlexiForce™ A301 Sensor available from Tekscan, Inc. (South Boston, Massachusetts). In certain embodiments, sensor 3800 is placed between sensor body element 3802 and sensor body element 3804 with the sensor being in contact with the body elements. Sensor body element 3802 and sensor body element 3804 may be non-conductive (e.g., plastic) elements.

FIG. 39 depicts a cross-sectional representation of an embodiment of force sensing element 3600 showing sensor 3800 sandwiched between sensor body element 3802 and sensor body element 3804 (e.g., the two non-conductive elements). Sensor body element 3802 and sensor body element 3804 are constructed and designed such that changes in force applied to force sensing element 3600 (e.g., tension caused by tightening or loosening strap 102 or tension caused by increasing/decreasing force applied from motors in the harness) causes changes in the load applied to sensor 3800 by the sensor body elements. For instance, sensor body element 3804 may move to or away from sensor 3800 based on the force applied to force sensing element 3600. The movement of sensor body element 3804 thus changes the force applied to sensor 3800 in response to changes in the force applied to force sensing element 3600. Accordingly, in certain embodiments, the load placed on sensor 3800 by the sensor body elements changes in accordance with the changes in the tension force applied to force sensing element 3600. In such embodiments, sensor 3800 is responsive to changes in force applied to force sensing element 3600 during use of wearable harness 900.

In certain embodiments, changes in the load placed on sensor 3800 may be detected as a change in resistance of the sensor. Resistance of sensor 3800 may be detected by a controller (such as controller 650 described herein) or another centralized processing component. The controller may then translate the resistance into a tension force for force sensing element 3600. The resistance of sensor 3800 may be detected from output provided at prongs 3806, shown in FIG. 38. Prongs 3806 may then be wired (e.g., by wires 3610, shown in FIG. 36) to the controller. Embodiments may also be contemplated where the resistance is detected wirelessly by the controller.

In various embodiments, the tension force measured for force sensing element 3600 is indicative of a tightness of fit for wearable harness 900 on a subject. The tightness of fit may include, for example, a tightness of the strapping of the wearable harness 900 to the subject. Adjustments based on the measurement of tightness through force sensing element 3600 may be made to adjust the comfort level of the subject while ensuring that there is enough tightness in wearable harness 900 such that the motors are effective in treating the subject when activated.

In certain embodiments, the tension force measured for force sensing element 3600 is correlated to the force of motors applied to the subject wearing wearable harness 900. For instance, as the tension in straps 120 and force sensing element 3600 increases, the perpendicular force of the motors against the body of the subject will increase accordingly. In other words, the tension forced measured for force sensing element 3600 can be correlated to the perpendicular force applied by the motors to the body of the subject. Thus, the tension force measured for force sensing element 3600 may be used as an indirect measure of the force applied by the motors.

In some embodiments, the tension force measured for force sensing element 3600 may be used to determine whether the subject is in compliance with a prescribed regimen for wearable harness 900. For example, the tension force may be monitored over time to determine if the subject is applied sufficient force from the motors over time periods determined by the prescribed regimen. The tension force measured for force sensing element 3600 may also be used to determine whether wearable harness 900 is being used properly. For instance, the tension force measured for force sensing element 3600 may be indicative of whether straps 120 are connected or not when the subject puts on wearable harness 900 to ensure the harness is being used properly. Other embodiments for compliance monitoring using force sensing element 3600 may also be contemplated based on the description herein.

In some embodiments, the tension force measured for force sensing element 3600 may be combined with other measurements or input factors. Other measurements may include, for example, measurements from other sensors such as capacitive sensors placed on wearable harness 900. Input factors may include subject property measurements such as, but not limited to, BMI, bust/chest size, body shape, gender, etc. The combination of the tension force measured for force sensing element 3600 with the other measurements or input factors may be implemented to determine a performance of wearable harness 900 in treating the subject (e.g., whether the wearable harness is treating the subject according to a prescribed regimen or the wearable harness is operating at appropriate levels). In some instances, the combination of the tension force measured for force sensing element 3600 with the other measurements or input factors may be implemented to improve fit of wearable harness 900, the comfort level of the subject in wearing the harness, and/or the clinical performance of the harness. For instance, proper fit and securement of wearable harness 900 on the subject (e.g., the right force is applied by the motors) may promote the proper performance of the harness in treating the subject (e.g., performance according to the prescribed regimen). Improving fit and comfort level may also lead to better compliance in use of wearable harness 900 and/or improve the clinical effectiveness of the harness. For example, the subject may be more likely to use wearable harness 900 if it fits comfortably.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system, comprising:
a wearable harness of a medical device positionable on a torso of a subject;
one or more straps coupled to the wearable harness for securing the wearable harness on the torso of the subject;
a plurality of engines coupled to the wearable harness, wherein the plurality of engines applies, during use, an oscillation force to at least one treatment area of the subject to mobilize a secretion in an airway within the subject substantially adjacent to the at least one treatment area;
at least one force sensing element integrated with a strap of the one or more straps, wherein the at least one force sensing element comprises:
a first non-conductive sensor body element comprising a first surface;
a second non-conductive sensor body element comprising a second surface facing the first surface of the first non-conductive sensor body element; and
a force sensor positioned between and in contact with the first and second surfaces of the first and second non-conductive sensor body elements,
wherein the force sensor has at least one property that changes with load applied to the force sensor by the first and second non-conductive sensor body elements in response to force applied to the at least one force sensing element from the strap, and
wherein the force sensor defines a plane disposed between the first and second surfaces of the first and second non-conductive sensor body elements such that the load applied by the non-conductive sensor body elements to the force sensor is applied substantially along the plane of the force sensor; and
a controller associated with the wearable harness, wherein the controller is configured to:
receive a measurement of the at least one property from the force sensor; and
determine a tension force applied to the at least one force sensing element by the strap based on the measurement of the at least one property.

2. The system of claim 1, wherein the at least one property is a resistance of the force sensor.

3. The system of claim 1, wherein at least one of the non-conductive elements is configured to move in response to a force applied to the at least one force sensing element, and wherein the movement of the at least one non-conductive element changes a force applied to the force sensor.

4. The system of claim 1, wherein the controller is configured to correlate the determined tension force applied to the at least one force sensing element with the oscillation force applied by the plurality of engines during use.

5. The system of claim 1, wherein the controller is configured to receive one or more additional inputs from one or more additional sensors coupled to the wearable harness, and determine a performance of the wearable harness in treating the subject.

6. The system of claim 5, wherein the controller is configured to determine the performance of the wearable harness in treating the subject based on one or more measurements of properties of the subject.

7. The system of claim 1, wherein the controller is configured to correlate the determined tension force applied to the at least one force sensing element with tension caused by increasing or decreasing force applied by the harness.

8. The system of claim 1, wherein at least a portion of the at least one force sensing element is attached to the wearable harness.

9. The system of claim 1, wherein the at least one force sensing element is attached to the strap.

10. The system of claim 1, wherein the one or more straps includes a first portion and a second portion coupled together using a connector to secure the wearable harness on the torso of the subject.

11. The system of claim 1, wherein the at least one force sensing element comprises a harness attachment portion coupled to the wearable harness.

12. The system of claim 1, wherein the at least one force sensing element comprises a strap attachment portion coupled to the strap using an opening defined by the strap attachment portion.

13. A method, comprising:

applying an oscillation force to at least one treatment area of a subject using a plurality of engines coupled to a wearable harness positioned on a torso of the subject, wherein the oscillation force mobilizes a secretion in an airway within the subject substantially adjacent to the at least one treatment area, wherein the wearable harness is secured on the torso of the subject using one or more straps;

receiving, at a controller coupled to the wearable harness, a measurement of at least one property from at least one force sensing element integrated with a strap of the one or more straps, wherein the at least one force sensing element comprises:

a first non-conductive sensor body element having a first surface;

a second non-conductive sensor body element having a second surface facing the first surface of the first non-conductive sensor body element; and a force sensor positioned between and in contact with the first and second surfaces of the first and second non-conductive sensor body elements, wherein the at least one property changes with load applied to the force sensor by the first and second non-conductive sensor body elements in response to force applied to the at least one force sensing element from the strap, and wherein the force sensor defines a plane disposed between the first and second surfaces of the first and second non-conductive sensor body elements such that the load applied by the non-conductive sensor body elements to the force sensor is applied substantially along the plane of the force sensor; and determining, by the controller, a tension force applied to the at least one force sensing element by the strap based on the measurement of the at least one property.

14. The method of claim 13, wherein the at least one property received at the controller is a resistance of the force sensor.

15. The method of claim 13, further comprising correlating, by the controller, the determined tension force applied to the at least one force sensing element with the oscillation force applied by the plurality of engines.

16. The method of claim 13, further comprising correlating, by the controller, the determined tension force applied to the at least one force sensing element with tension caused by tightening or loosening the strap.

17. The method of claim 13, further comprising determining, by the controller, a performance of the wearable harness in treating the subject based on the determined tension force applied to the at least one force sensing element and one or more additional inputs.

18. The method of claim 17, wherein the one or more additional inputs includes at least one of either a measurement from at least one additional sensor coupled to the wearable harness or a measurement of at least one property of the subject.

19. The method of claim 13, further comprising determining, by the controller, a fit of the wearable harness on the torso of the subject based on the determined tension force applied to the at least one force sensing element.

20. The method of claim 13, further comprising determining, by the controller, whether the subject is using the wearable harness in compliance with a prescribed regimen based on the determined tension force applied to the at least one force sensing element.

* * * * *